US005994012A

United States Patent [19]
Watanabe et al.

[11] Patent Number: 5,994,012
[45] Date of Patent: Nov. 30, 1999

[54] NAPHTHOQUINONE DERIVATIVE AND ELECTROPHOTOSENSITIVE MATERIAL USING SAME

[75] Inventors: Yukimasa Watanabe; Sakae Saito; Hirofumi Kawaguchi; Akiyoshi Urano; Fumio Sugai; Atsushi Fujii; Yasufumi Mizuta; Toshiyuki Fukami; Ichiro Yamazato; Yuji Tanaka; Eiichi Miyamoto; Hideo Nakamori; Mitsuo Ihara, all of Osaka, Japan

[73] Assignee: Mita Industrial Co., Ltd., Osaka, Japan

[21] Appl. No.: 08/937,448

[22] Filed: Sep. 25, 1997

Related U.S. Application Data

[62] Division of application No. 08/709,040, Sep. 6, 1996, Pat. No. 5,863,688.

[30]     Foreign Application Priority Data

Sep. 25, 1995   [JP]   Japan ..................................... 7-246347
Apr. 18, 1996   [JP]   Japan ..................................... 8-96538

[51] Int. Cl.[6] .............................. G03G 5/047; G03G 5/09
[52] U.S. Cl. ......................... 430/58.25; 430/83; 430/132; 430/133
[58] Field of Search ........................... 430/72, 83, 58.25, 430/132, 133

[56]                 References Cited

U.S. PATENT DOCUMENTS

| | | | |
|---|---|---|---|
| 4,869,985 | 9/1989 | Kung et al. | 430/58.25 |
| 4,909,966 | 3/1990 | Kung et al. | 430/58.25 |
| 4,921,637 | 5/1990 | Kung et al. | 430/58.25 |
| 5,718,997 | 2/1998 | Hayata et al. | 430/83 |
| 5,863,688 | 1/1999 | Watanabe et al. | 430/72 |

FOREIGN PATENT DOCUMENTS

| | | |
|---|---|---|
| 0088607 | 9/1983 | European Pat. Off. . |
| 0449565 | 10/1991 | European Pat. Off. . |

OTHER PUBLICATIONS

McMurry, "Organic Chemistry", pp. 88–91.
Watanabe, et al., "An Annulation Reaction to Naphthalene–1, 4–diols, Using Dimethyl Phthalide–3–phosphonates", Chem. Pharm., Bull., pp. 968–970.
Shcherban et al., "Synthesis of 2–aryl–3–hydroxy–1, 4 naphthoquinones via 2, 2–disubstited 1, 3–inandiones", pp. 342–245.
Sharma, Subhash C. and Torssell, Kurt, "Alkoxycarbonylation of Quinones. A Route to Naphthacene Quinones. Reversibility in Homolytic Substitution", Acta Chem. Scand. B, vol. 32, No. 5, 347–353.
Japanese Patent Laid–Open Publication 01206349, Aug. 18, 1989.
Japanese Patent Laid–Open Publication 06110227, Apr. 22, 1994.
Ozola, E., et al., Abstract of Synthesis of Acyl–1, 4–Napthoquinones Based on 1, 3–Indandione, Chemical Abstracts, vol. 68, No. 17, p. 7523, Apr. 22, 1968.
Zalukaev, L.P., et al., Abstract of "Synthesis of 2, 3–disubstituted 1, 4–naphthoquinones via 1, 3–inandiones," Chemical Abstracts, vol. 85, no. 5, p. 367, Aug. 2, 1976.
Kloc, K., et al., Abstract of "Synthesis of (3, 3–dimethyloxiranyl) quinones and (dimethylacetyl quinones as potential cytostatics," Chemical Abstracts, vol. 107, No. 21, p. 702, Nov. 23, 1987.
Torsell, K., et al., Abstract of "Alkoxycarbonylation of Quinones. A Route to Naphthacene Quinones. Reversibility in Homolytic Substitution," Acta Chemica Scandinavia, Series B—Organic Chemistry and Biochemistry, vol. B32, No. 5, pp. 347–353, 1978.
Yannoni, C. S., et al., "An Organotransition–Metal Synthesis of Naphthoquinones," Journal of the American Chemical Society, vol. 102, No. 24, pp. 7397–7398, 1980.
Giles, R. G. F., et al., Abstract of "Synthesis of the Alphin–Related (+/−)–7, 9–Dideoxyquinone A and (+/−)–7,9 Diodeoxyquinone A," Journal of the Chemical Society, Perkin Transactions 1, No. 6, pp. 1249–1254, 1983.
Balbanov, E.M., et al., Abstract of "Study of the Electrophotograhic Sensitivity and Photoconductivity of Poly (N–vinylcarbazole) and Poly (N–epoxypropylcarbazole) Films doped with Some Derivatives of Naphthoquinone," Chemical Abstracts, vol. 94.
Schäfer, W., et al., "Über die Oxidative Aminierung von 1', 4'–Dihydroxy–2'–Acetonapthon,"Liebegs Der Chemie., No. 4, pp. 503–521, 1979.
Larinya, L., et al., "Intramolecular Donor–Acceptor Complexes of 2–Phenyl–1, 4–Naphthoquinone Series," Journal of Organic Chemistry of the USSR, vol. 20, No. 9, pp. 1748–1752, Sep. 1984.

(List continued on next page.)

Primary Examiner—Roland Martin
Attorney, Agent, or Firm—Smith, Gambrell & Russell

[57]                 ABSTRACT

The present invention provides a naphthoquinone derivative represented by the general formula (I):

(1)

$$\text{naphthoquinone with } R^1 \text{ and } C(=O)R^2 \text{ substituents}$$

wherein $R^1$ and $R^2$ are as defined in the specification. An electrophotosensitive material containing this naphthoquinone derivative as an electron transferring material has high sensitivity.

20 Claims, 9 Drawing Sheets

OTHER PUBLICATIONS

Lokmane, E., et al. Abstract of "Synthesis and properties Charge–transfer complexes and auto complexes. XXXI. Study of donor acceptor systems, 4–naphthoquionone derivatives," Chemical Abstracts, vol. 90, No. 23, pp. 576–577, Jun. 4, 1979.

Lokmane, E., et al., Abstract of "Synthesis and properties of complexes and auto complexes with charge transfer. XX. 2–Aryl–3–(N, N–alkylarylamino) acetyl–1, 4–naphthoquinones–auto complexes with a three–membered bridge," Chemical Abstracts, vol. 88, No. 13, p. 497, Mar. 27, 1978.

Ozola, et al., Abstract of "Synthesis of acyl–1, 4–naphthoquinones based on 1, 3–indandione," Chemical Abstracts, vol. 68, No. 17, p. 7523, Apr. 1968.

Koelsch, B., et al., "A Synthesis of Substituted alpha–Naphthoquinones,"0 Journal of the American Chemical Society, vol. 62, p. 561, 1940.

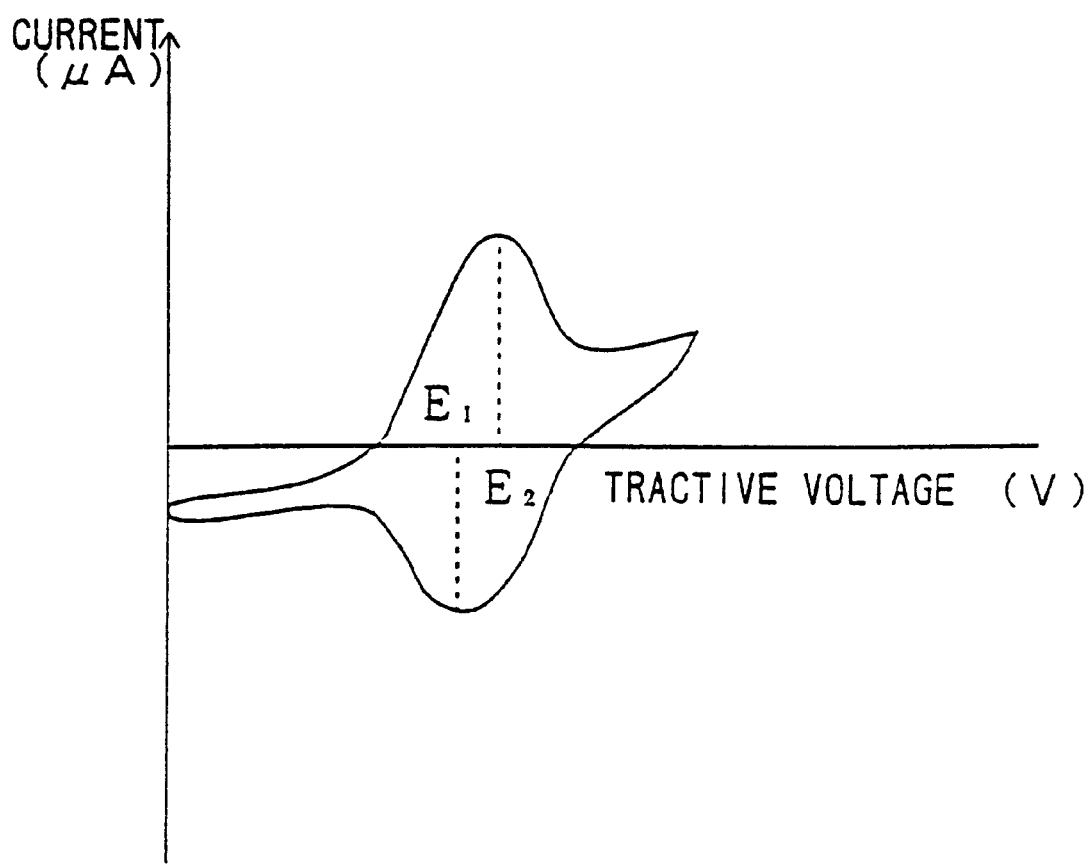
F I G. 1

NAPHTHOQUINONE DERIVATIVE AND ELECTROPHOTOSENSITIVE MATERIAL USING SAME

This is a divisional of co-pending application Ser. No. 08/709,040 filed on Sep. 6, 1996, now U.S. Pat. No. 5,863,688.

BACKGROUND OF THE INVENTION

1. Field of the Invention

The present invention relates to a novel naphthoquinone derivative, and an electrophotosensitive material using the same.

2. Description of the Prior Art

In image forming apparatuses such as electrostatic copying machines, laser printers and facsimile devices for normal papers, there is widely used an electrophotosensitive material, especially so-called as an organic photosensitive material, comprising a conductive substrate and a photosensitive layer containing an electric charge generating material which generates an electric charge due to light irradiation, an electric charge transferring material which transfers the electric charge generated and a binding resin in which these substances are dispersed, the photosensitive layer being provided on the conductive substrate.

The organic photosensitive material is classified roughly into a single-layer photosensitive material wherein an electric charge generating material and an electric charge transferring material are contained in the same layer and a multi-layer photosensitive material comprising an electric charge generating layer containing an electric charge generating material and an electric charge transferring layer containing an electric charge transferring material, which are mutually laminated. Among these, the multi-layer photosensitive material is conventionally employed. In a conventional normal multi-layer photosensitive material, an electric charge generating layer and an electric charge transferring layer having a film thickness larger than that of the electric charge generating layer are generally provided on the surface of a conductive layer in this order in view of a mechanical strength.

The electric charge transferring material include hole transferring material and electron transferring material. Among electric charge transferring materials which are known at present, almost all of electric charge transferring materials having a high carrier mobility are hole transferring materials. Therefore, when the photosensitive material, which is put into practical use, is the multi-layer photosensitive material wherein the electric charge transferring material is provided on the surface side, it becomes a negative charging type photosensitive material.

However, it is necessary that the negative charging type multi-layer photosensitive material is charged by negative-polarity corona discharge which generates large amount of ozone. Thus, there are problems such as influence of ozone on environment and deterioration of photosensitive material itself.

In order to solve these problems, an electron transferring material having a high carrier mobility has been developed and studied. In Japanese Laid-Open Patent Publication No. 1-206349, there is suggested that a compound having a diphenoquinone structure is used as the electron transferring material.

However, diphenoquinones are generally inferior in compatibility with a binding resin and are not uniformly dispersed in the binding resin so that a hopping distance of electrons becomes large and transfer of electrons in the low electric field does not easily arise. Therefore, diphenoquinones themselves have a high carrier mobility. However, when using them for the photosensitive material as the electron transferring material, characteristics thereof are not sufficiently developed and a residual potential of the photosensitive material becomes high, which results in insufficient photosensitivity.

As described above, almost all of organic photosensitive materials, which are put into practical use, are multi-layer photosensitive materials. However, the single-layer photosensitive material has a lot of advantages that it has a simple structure, can be easily produced in comparison with the multi-layer photosensitive material, and can inhibit formation of membrane defects to improve optical characteristics. Besides, when using the electron transferring material and hole transferring material in combination as the electric charge transferring material, one single-layer photosensitive material can be used for both positive and negative charging type photosensitive materials, thereby widening the application range of the photosensitive material. However, the above diphenoquinones have a problem that transferring of electrons and holes are inhibited by an interaction between the diphenoquinones and hole transferring material. Therefore, such a single-layer photosensitive material has never been put into practical use at present.

SUMMARY OF THE INVENTION

It is a main object of the present invention to provide a novel naphthoquinone derivative which has excellent electron transferring properties and compatibility with binding resin, thereby being useful as an electron transferring material, and a high-sensitive electrophotosensitive material using the same.

It is another object of the present invention to provide a high-sensitive single-layer electrophotosensitive material which can be used for both positive and negative charging type electrophotosensitive materials.

It is still another object of the present invention to provide an electrophotosensitive material having a high sensitivity and an excellent wear resistance.

The naphthoquinone derivative of the present invention is represented by the general formula (1):

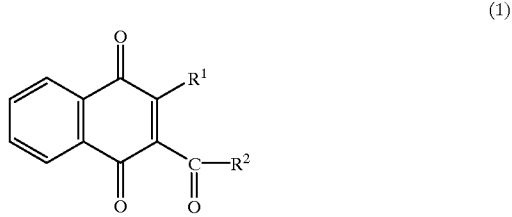

(1)

wherein $R^1$ is an alkyl group which may have a substituent, or an aryl group which may have a substituent; and $R^2$ is an alkyl group which may have a substituent, an aryl group which may have a substituent, or a group represented by the following formula (1a):

(1a)

wherein $R^3$ is an alkyl group which may have a substituent, or an aryl group which may have a substituent.

The electrophotosensitive material of the present invention comprises a conductive substrate, and a photosensitive layer containing the naphthoquinone derivative represented by the general formula (1), the photosensitive layer being provided on the conductive substrate.

The naphthoquinone derivative of the present invention is superior in electron acceptive properties due to an action of a carbonyl group >C=O substituted on a naphthoquinone ring and is also superior in solubility in solvent and a compatibility with binding resin due to an action of an alkyl or aryl group substituted on the naphthoquinone ring. Therefore, the naphthoquinone derivative of the present invention is superior in matching with electric charge generating material (e.g., pigment). Hence, injection of electrons from the electric charge generating material to the naphthoquinone derivative is smoothly conducted. The naphthoquinone derivative is uniformly dispersed in the photosensitive layer so that the hopping distance of electrons is short, and is particularly superior in electron transferring properties in the low electric field. Accordingly, the electrophosensitive material of the present invention containing the naphthoquinone derivative (1) as the electron transferring material in the photosensitive layer, has a high sensitivity.

The naphthoquinone derivative (1) does not cause an interaction with the hole transferring material, and therefore does not inhibit transferring of electrons and holes. Hence, a photosensitive material having a single-layer photosensitive layer wherein the hole transferring material is contained together with the napthoquinone derivative (1), shows a high sensitivity.

When an electron acceptive compound having a redox (an oxidation-reduction) potential of –0.8 to –1.4 V is contained in the photosensitive layer, together with the naphthoquinone derivative (1), the electron acceptive compound serves to draw electrons from the electric charge generating material and transfer them to the naphthoquinone derivative (1). Therefore, injection of electrons from the electric charge generating material into the naphthoquinone derivative becomes more smooth and the sensitivity of the photosensitive material is further improved.

The naphthoquinone derivative (1) of the present invention can also be used for, for example, solar batteries, organic electroluminescence devices, as well as the electrophotosensitive material, by utilizing its high electron transferring capability.

BRIEF DESCRIPTION OF THE DRAWINGS

FIG. 1 is a graph illustrating a relationship between the traction voltage (V) and current ($\mu$A) for determining the redox potential of the electron acceptive compound.

DETAILED DESCRIPTION OF THE INVENTION

Figure 2:
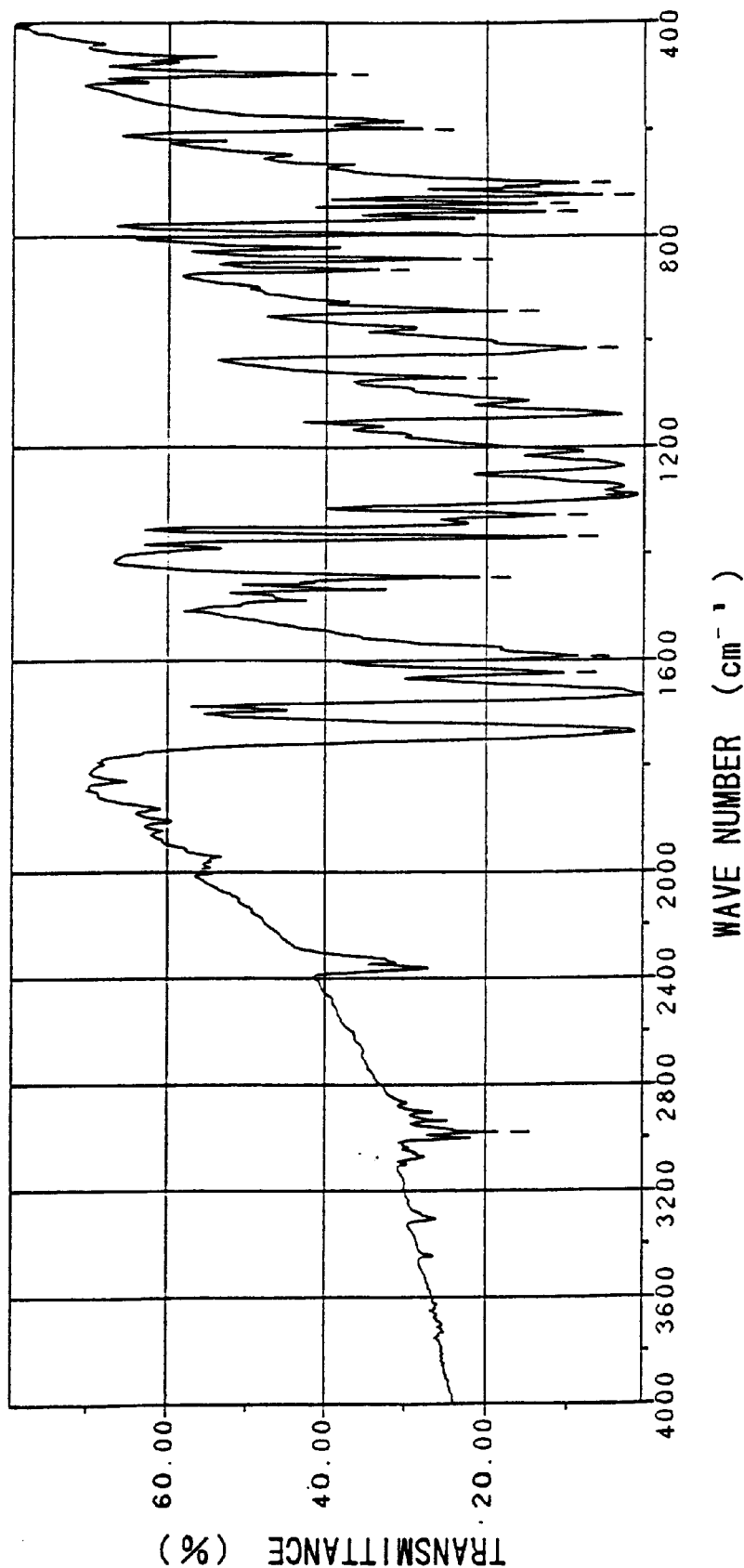
FIG. 2 is a graph illustrating an infrared absorption spectrum of the product synthesized in Synthetic Example 1.

Among the naphthoquinone derivatives (1) of the present invention, the naphtoquinone derivative wherein the group $R^2$ in the above general formula (1) is represented by the formula (1a):

$$-O-R^3 \quad (1a)$$

that is, the naphthoquinone derivative represented by the general formula (10):

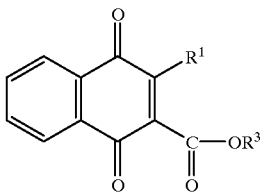

(10)

wherein $R^1$ and $R^2$ are as defined above will be explained.

Examples of the alkyl group corresponding to the groups $R^1$ and $R^3$ in the general formula (10) include alkyl groups having 1 to 6 carbon atoms, such as methyl, ethyl, normal propyl, isopropyl, normal butyl, isobutyl, secondary butyl, tertiary butyl, pentyl, hexyl, etc.

The above alkyl groups may have a substituent, and examples of the substituent include halogen atoms such as fluorine, chlorine, bromine and iodine or the following aryl groups.

Examples of the aryl group corresponding to the groups $R^1$ and $R^3$ include phenyl, tolyl, xylyl, biphenyl, o-terphenyl, naphthyl, anthryl, phenanthryl, etc.

The above aryl groups may have a substituent, and examples of the substituent include the above alkyl groups and halogen atoms.

The naphthoquinone derivative represented by the above general formula (10) wherein the group $R^3$ is an alkyl group is particularly superior in electron transferring capability, and a photosensitive material having a higher sensitivity is obtained. When an aryl group as a substituent is substituted on the above alkyl group, a high glass transition Tg, Tg of the photosensitive layer can be improved and, for example, it has an effect of preventing a dent from forming on the photosensitive material at the time of stopping the device by using a cleaning blade which pressures on the surface of the photosensitive material.

Since the naphthoquinone derivative wherein the above group $R^3$ is an aryl group has a high glass transition Tg, Tg of the photosensitive layer can be improved, thereby obtaining the same effect of preventing a dent from forming on the photosensitive material at the time of stopping the device, as described above. The naphthoquinone derivative wherein an alkyl group as a substituent is substituted to the above aryl group is particularly superior in solubility in solvent and compatibility with binding resin.

In order to synthesize the naphthoquinone derivative represented by the general formula (10), a 1,3-indandione derivative represented by the general formula (1b):

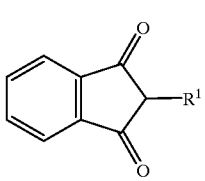

(1b)

is reacted with a bromoacetic ester represented by the general formula (1c):

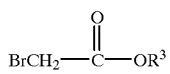
(1c)

to synthesize an acetic ester derivative represented by the general formula (1d):

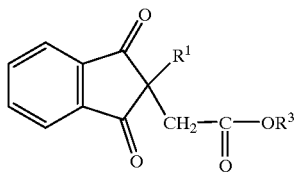
(1d)

Then, the acetic ester derivative (1d) is isomerized in the presence of sodium hydride to synthesize a β-naphthoic ester derivative represented by the general formula (1e):

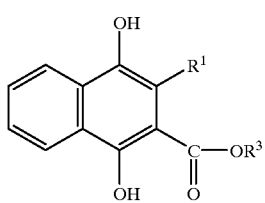
(1e)

which is oxidized to obtain the naphthoquinone derivative represented by the general formula (10):

(10)

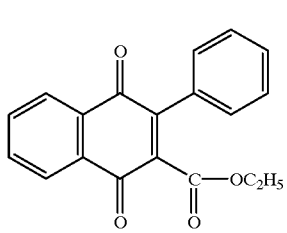

wherein $R^1$ and $R^3$ are as defined above.

Examples of the naphthoquinone derivative (10) wherein the group $R^3$ is an alkyl group which may have a substituent include compounds represented by the formulas (10-1) to (10-4):

(10-1)

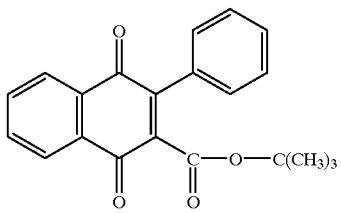

(10-2)

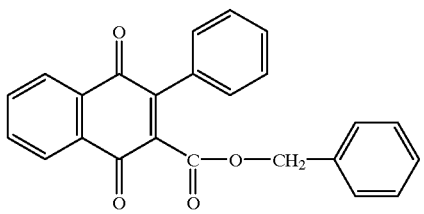

(10-3)

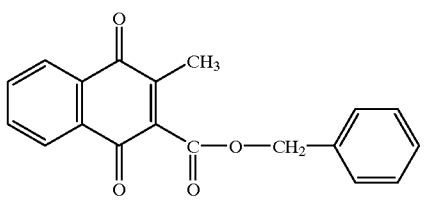

(10-4)

Examples of the naphthoquinone derivative (10) wherein the group $R^3$ is an aryl group which may have a substituent include compounds represented by the formulas (10-5) to (10-7):

(10-5)

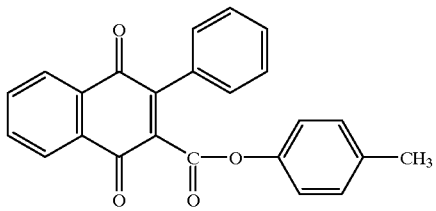

(10-6)

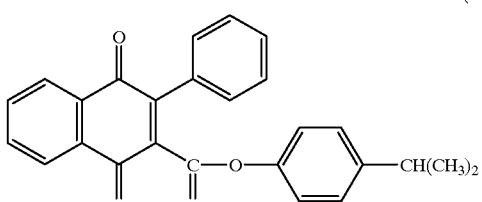

(10-7)

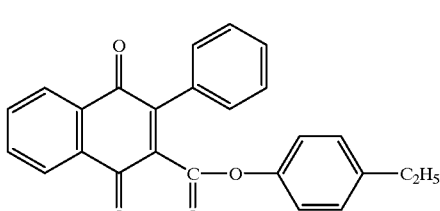

Then, the naphthoquinone derivative represented by the above general formula (1) wherein the group $R^2$ is not the group represented by the formula (1a) but an alkyl group which may have a substituent or an aryl group which may have a substituent will be described.

The above naphthoquinone derivative is particularly stable to ultraviolet light, and therefore a photosensitive material excellent in light resistance can be obtained.

Examples of the above alkyl group include the same groups as those described above. Examples of the substituent which may be substituted on the above alkyl group include the same halogen atoms and aryl groups as those described above.

Examples of the aryl group include the same groups as those described above. Examples of the substituent which may be substituted on the above aryl group include the same halogen atoms and alkyl groups as those described above.

Since the naphthoquinone derivative wherein the above group $R^2$ is an aryl group has a high glass transition Tg, Tg of the photosensitive layer can be improved, thereby showing the same effect of preventing a dent from forming on the photosensitive material at the time of stopping the device, as described above.

In order to synthesize the above naphthoquinone derivative, the 1,3-indandione derivative represented by the above general formula (1b) is reacted with a bromoacetone derivative represented by the general formula (1f):

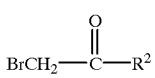
(1f)

to synthesize a ketone represented by the general formula (1g):

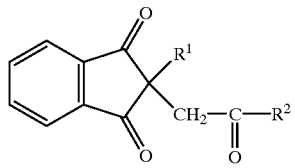
(1g)

wherein $R^1$ and $R^2$ are as described above.

Then, the above ketone derivative (1g) is isomerized in the presence of sodium hydride to synthesize a β-naphthoyl derivative represented by the general formula (1h):

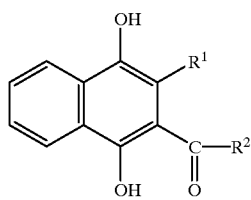
(1h)

which is oxidized to obtain the naphthoquinone derivative represented by the general formula (1), wherein the group $R^2$ is an alkyl group which may have a substituent, or an aryl group which may have a substituent.

Examples of the above naphthoquinone derivative include compounds represented by the formulas (1-1) to (1-4):

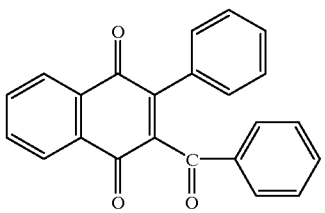
(1-1)

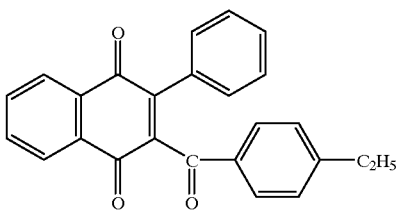
(1-2)

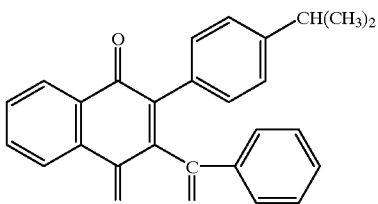
(1-3)

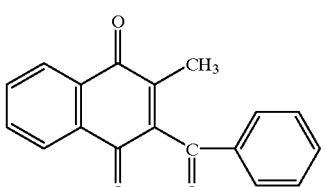
(1-4)

The electrophotosensitive material of the present invention will be described.

The electrophotosensitive material of the present invention comprises a conductive substrate and a photosensitive layer containing one or more naphthoquinone derivatives represented by the above general formula (1) (including that represented by the general formula (10), as a matter of course) as an electron transferring material, the photosensitive layer being provided on the conductive layer.

The photosensitive layer is classified into a single-layer type photosensitive layer and a multi-layer type photosensitive layer, as described above.

The single-layer type photosensitive layer is obtained by containing the naphthoquinone derivative (1) of the present invention as an electron transferring material, a hole transferring material and an electric charge generating material in a binding resin, and a photosensitive material having this single-layer type photosensitive layer can be used for both positive and negative charging type photosensitive materials. It is preferred to use for the positive charging type photosensitive material which does not require the use of the above-described negative corona discharge.

The multi-layer type photosensitive layer comprises an electric charge generating layer containing an electric charge generating material and an electric charge transferring layer containing the naphthoquinone derivative (1) of the present invention as an electron transferring material, and a photosensitive material comprising this multi-layer type photosensitive layer can produce positive and negative charging type photosensitive materials by changing the order of laminating both layers. It is preferred to produce the positive charging type photosensitive material whose electric charge transferring layer is arranged at the outermost layer for the same reason as in a single layer type.

The present invention is applicable for the above both single-layer and multi-layer photosensitive materials. The single-layer photosensitive material is particularly preferred for the following reasons. That is, the single-layer photosensitive material can be used for both positive and negative charging type photosensitive materials as described above, and can be easily produced because of its simple structure. Furthermore, the single-layer photosensitive material can inhibit formation of membrane defects when laminating a layer on the previously formed layer, and can improve optical characteristics because of little interface between layers.

In the positive charging type photosensitive material comprising the single-layer photosensitive layer, electrons (−) emitted from the electric charge generating material in the exposure process are smoothly injected into the naphthoquinone derivative (1), and then transferred to the surface of the photosensitive layer by means of the giving and receiving of electrons between the naphtoquinone derivatives (1) to cancel a positive electric charge (+) which has previously been charged on the surface of the photosensitive layer.

On the other hand, holes (+) are injected into the hole transferring material and then transferred to the conductive substrate by means of the giving and receiving of holes between the hole transferring materials to cancel a negative electric charge (−) which has previously been charged on the conductive substrate.

During this time, the naphthoquinone derivative (1) and hole transferring material causes no interaction as described above, and therefore, holes (+) and electrons (−) are efficiently and rapidly transferred without being trapped on the way. It is considered that the sensitivity of the photosensitive material is improved in this manner.

In the photosensitive material of the present invention, it is preferred to use the naphthoquinone derivative (1) in combination with the electron acceptive compound having a traction potential of −0.8 to −1.4 V, as described above.

The above electron acceptive compound serves to draw electrons from the electric charge generating material when forming an electron-hole pair using the electric charge generating material by light irradiation because the energy level of LUMO (Lowest Unoccupied Molecular Orbital) of the electron acceptive compound is lower than that of the electric charge generating material. Therefore, the proportion of disappearance of electrons and holes due to recombination of electrons and holes in the electric charge generating material decreases and the electric charge generating efficiency is improved.

The electron acceptive compound also serve to efficiently transfer electrons drawn from the electric charge generating material to the naphthoquinone derivative as the electron transferring material. In the system using the electron acceptive material in combination with the electron transferring material, injection and transfer of electrons from the electric charge generating material to the electron transferring material are smoothly conducted and the sensitivity of the photosensitive material is further improved.

The reason for limiting the traction potential of the electron acceptive compound within the above range is as follows.

That is, when the electron acceptive compound has a traction potential of lower than −0.8 V, electrons transferring while repeatedly causing trapping-detrapping are fallen into the level where detrapping can not be effected to cause carrier trapping. Therefore, transferring of electrons are prevented, which results in decrease in sensitivity of the photosensitive material.

To the contrary, when the electron acceptive compound has a traction potential of higher than −1.4 V, the energy level of LUMO becomes higher than that of the electric charge generating material. When the electron-hole pair is formed, the electron acceptive compound does not serve to draw electrons from the electric charge generating material, which fails to improve the electric charge-generating efficiency. As a result, the sensitivity of the photosensitive material is decreased.

It is particularly preferred that the traction potential of the electron acceptive compound is from −0.85 to −1.00 V within the above range.

The traction potential will be measured by means of a three-electrode system cyclic voltametry using the following materials.

Electrode:

Work electrode (glassy carbon electrode),

Counter electrode (platinum electrode)

Reference electrode: silver nitrate electrode (0.1 mol/l $AgNO_3$-acetonitrile solution)

Measuring solution:

Electrolyte: tetra-n-butylammonium perchlorate (0.1 mols)

Measuring substance: electron acceptive compound (0.001 mols)

Solvent: $CH_2Cl_2$ (1 litter)

The above materials are mixed to prepare a measuring solution. As shown in FIG. 1, a relation between the traction voltage (V) and current ($\mu$A) is determined to measure $E_1$ and $E_2$ shown in the same figure, and then the traction potential is determined according to the following calculation formula:

$$\text{Traction potential} = (E_1 + E_2)/2 (V)$$

The electron acceptive compound may be any compound having electron acceptive properties and a traction potential within the range from −0.8 to −1.4 V, and is not specifically limited. It is possible to select the compound having a traction potential within the above range from compounds having electron acceptive properties, for example, benzoquinone compound, naphthoquinone compound, anthraquinone compound, diphenoquinone compound, malononitrile compound, thiopyran compound, 2,4,8-trinitrothioxanthone, fluorenone compound such as 3,4,5,7-tetranitro-9-fluorenone, dinitroanthracene, dinitroacridine, nitroanthraquinone and dinitroanthraquinone.

Among these, there can be suitably used a compound having a traction potential within the above range, which belongs to a benzoquinone compound represented by the general formula (2):

(2)

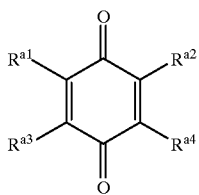

wherein $R^{a1}$, $R^{a2}$, $R^{a3}$ and $R^{a4}$ are the same or different and indicate a hydrogen atom, an alkyl group, an alkoxy group, an aryl group, an aralkyl group, a cycloalkyl group, or an amino group which may have a substituent, or a diphenoquinone compound represented by the general formula (3):

(3)

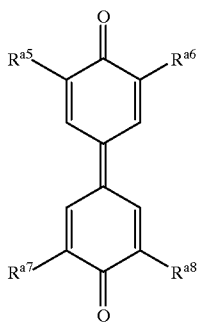

wherein $R^{a5}$, $R^{a6}$, $R^{a7}$ and $R^{a8}$ are the same or different and indicate a hydrogen atom, an alkyl group, an alkoxy group, an aryl group, an aralkyl group, a cycloalkyl group, or an amino group which may have a substituent.

Examples of the alkyl group include the same groups as those described above. Examples of the aralkyl group include benzyl, benzhydryl, trityl and phenethyl. Examples of the alkoxy group include alkoxy groups having 1 to 6 carbon atoms, such as methoxy, ethoxy, n-propoxy, iso-propoxy, t-butoxy, pentyloxy and hexyloxy. Examples of the aryl group include phenyl and naphthyl. Examples of the cycloalkyl group include cycloalkyl groups having 3 to 6 carbon atoms, such as cyclopropyl, cyclobutyl, cyclopentyl and cyclohexyl. Examples of the amino group which may have a substituent, include amino, monomethylamino, dimethylamino, monoethylamino and diethylamino.

Specific examples of the benzoquinone compound include p-benzoquinone represented by the formula (2-1) (traction potential: −0.81 V), and 2,6-di-t-butyl-p-benzoquinone represented by the formula (2-2) (traction potential: −1.31 V).

(2-1)

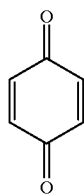

(2-2)

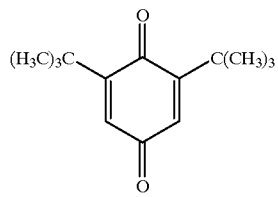

Specific examples of the diphenoquinone compound include 3,5-dimethyl-3',5'-di-t-butyl-4,4'-diphenoquinone represented by the formula (3-1)(traction potential: −0.86 V), and 3,5,3',5'-tetrakis(t-butyl)-4,4'-diphenoquinone represented by the formula (3-2)(traction potential: −0.94 V), but are not limited thereto.

(3-1)

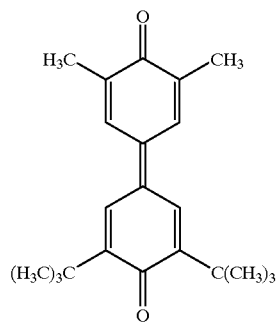

(3-2)

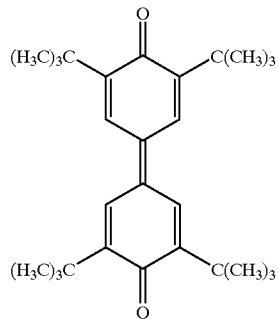

These electron acceptive compounds can be used alone or in combination thereof.

Various materials used for the electrophotosensitive material of the present invention will be described.

Hole Transferring Material

Examples of the hole transferring material include compounds represented by the general formulas (HT-1) to (HT-13):

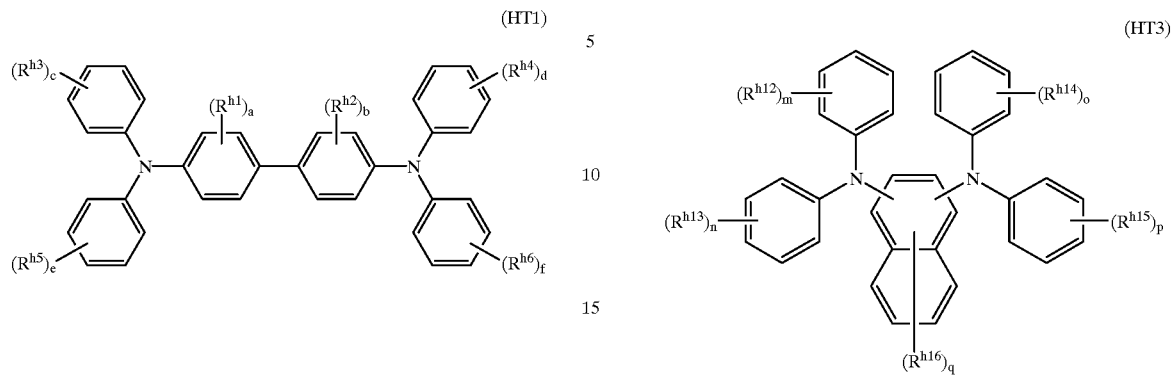

(HT1)

wherein $R^{h1}$, $R^{h2}$, $R^{h3}$, $R^{h4}$, $R^{h5}$ and $R^{h6}$ are the same or different and indicate a hydrogen atom, a halogen atom, an alkyl group which may have a substituent, an alkoxy group which may have a substitutent, or an aryl group which may have a substituent; a and b are the same or different and indicate an integer of 1 to 4, and c, d, e and f are the same or different and indicate an integer of 1 to 5, provided that when a, b, c, d, e or f is not less than 2, plural groups represented by $R^{h1}$, $R^{h2}$, $R^{h3}$, $R^{h4}$, $R^{h5}$ or $R^{h6}$ may be different,

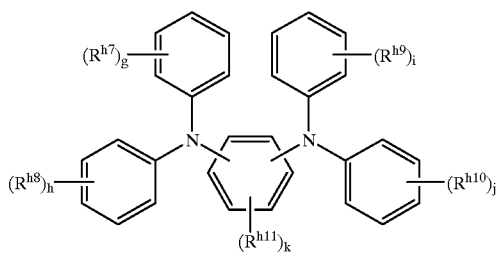

(HT2)

wherein $R^{h7}$, $R^{h8}$, $R^{h9}$, $R^{h10}$ and $R^{h11}$ are the same or different and indicate a hydrogen atom, a halogen atom, an alkyl group which may have a substituent, an alkoxy group which may have a substitutent, or an aryl group which may have a substituent; g, h, i and j are the same or different and indicate an integer of 1 to 5; and k is an integer of 1 to 4, provided that when g, h, i, j or k is not less than 2, plural groups represented by $R^{h7}$, $R^{h8}$, $R^{h9}$, $R^{h10}$ or $R^{h11}$ may be different wherein $R^{h12}$, $R^{h13}$, $R^{h14}$ and $R^{h15}$ are the same or different and indicate a hydrogen atom, a halogen atom, an alkyl group which may have a substituent, an alkoxy group which may have a substituent, or an aryl group which may have a substituent; $R^{h16}$ is a hydrogen atom, a halogen atom, a cyano group, a nitro group, an alkyl group which may have a substituent, an alkoxy group which may have a substitutent or an aryl group which may have a substituent; m, n, o and p are the same or different and indicate an integer of 1 to 5; and q is an integer of 1 to 6, provided that when m, n, o, p or q is not less than 2, plural groups represented by $R^{h12}$, $R^{h13}$, $R^{h14}$, $R^{h15}$ or $R^{h16}$ may be different

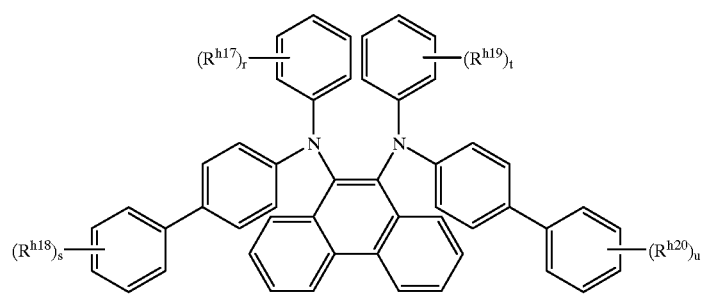

(HT4)

wherein $R^{h17}$, $R^{h18}$, $R^{h19}$ and $R^{h20}$ are the same or different and indicate a hydrogen atom, a halogen atom, an alkyl group which may have a substituent, an alkoxy group which may have a substitutent, or an aryl group which may have a substituent; and r, s, t and u are the same or different and indicate an integer of 1 to 5, provided that when r, s, t or u is not less than 2, plural groups represented by $R^{h17}$, $R^{h18}$, $R^{h19}$ or $R^{h20}$ may be different.

(HT5)

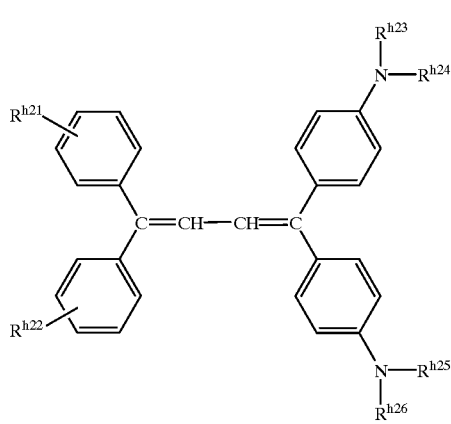

wherein $R^{h21}$ and $R^{h22}$ are the same or different and indicate a hydrogen atom, a halogen atom, an alkyl group or an alkoxy group; and $R^{h23}$, $R^{h24}$, $R^{h25}$ and $R^{h26}$ may be the same or different and indicate a hydrogen atom, an alkyl group or an aryl group, (HT6)

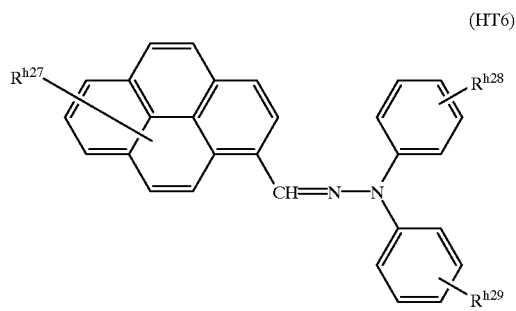

wherein $R^{h27}$, $R^{h28}$ and $R^{h29}$ are the same or different and indicate a hydrogen atom, a halogen atom, an alkyl group or an alkoxy group, (HT7)

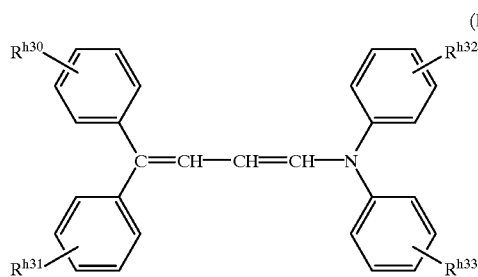

wherein $R^{h30}$, $R^{h31}$, $R^{h32}$ and $R^{h33}$ are the same or different and indicate a hydrogen atom, a halogen atom, an alkyl group or an alkoxy group, (HT8)

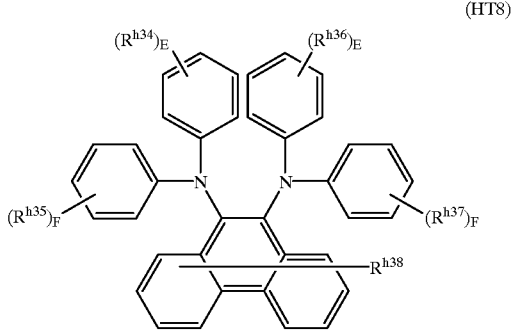

wherein $R^{h34}$, $R^{h35}$, $R^{h36}$ and $R^{h37}$ are the same or different and indicate a halogen atom, an alkyl group, an aryl group, an aralkyl group, or an alkoxy group; $R^{h38}$ indicates a hydrogen atom, a halogen atom, an alkyl group, or an alkoxy group; and E and F indicate an integer of 0 to 2, (HT9)

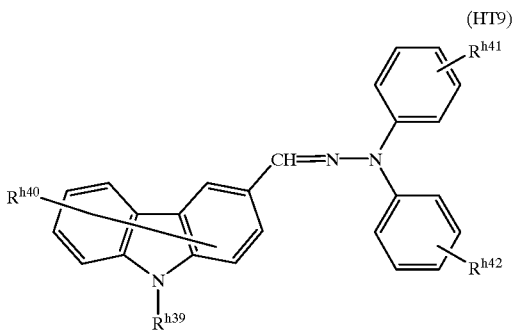

wherein $R^{h39}$ is a hydrogen atom, or an alkyl group; and $R^{h40}$, $R^{h41}$ and $R^{h42}$ are the same or different and indicate a hydrogen atom, a halogen atom, an alkyl group or an alkoxy group, (HT10)

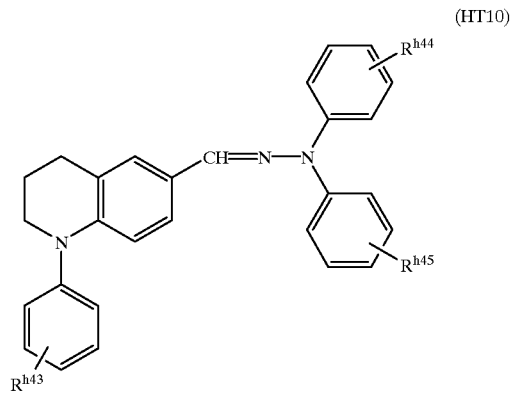

wherein $R^{h43}$, $R^{h44}$ and $R^{h45}$ are the same or different and indicate a hydrogen atom, a halogen atom, an alkyl group or an alkoxy group, (HT11)

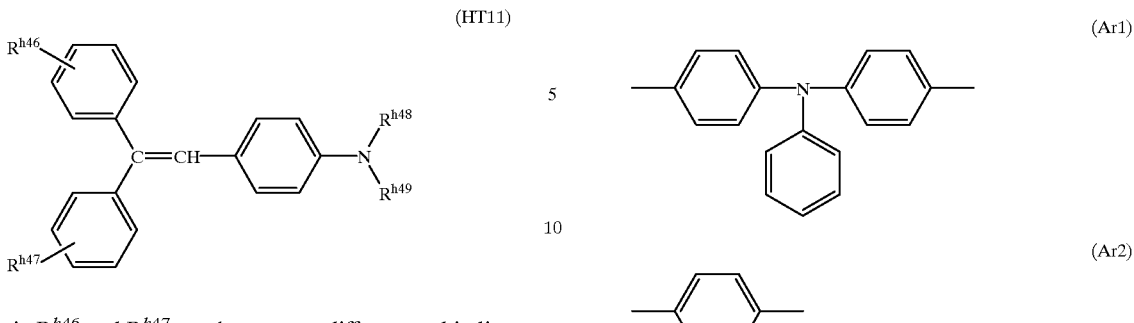
(Ar1)

(Ar2)

wherein $R^{h46}$ and $R^{h47}$ are the same or different and indicate a hydrogen atom, a halogen atom, an alkyl group which may have a substituent or an alkoxy group which may have a substituent; and $R^{h48}$ and $R^{h49}$ are the same or different and indicate a hydrogen atom, an alkyl group which may have a substituent, or an aryl group which may have a substituent,

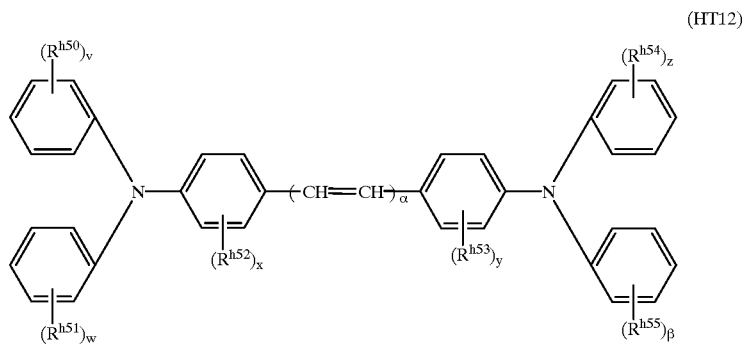
(HT12)

wherein $R^{h50}$, $R^{h51}$, $R^{h52}$, $R^{h53}$, $R^{h54}$ and $R^{h55}$ are the same or different and indicate a hydrogen atom, an alkyl group which may have a substituent, an alkoxy group which may have a substituent, or an aryl group which may have a substituent; $\alpha$ is an integer of 1 to 10; and v, w, x, y, z and $\beta$ are the same or different and indicate 1 or 2, provided that when v, w, x, y, z or $\beta$ is 2, both groups represented by $R^{h50}$, $R^{h51}$, $R^{h52}$, $R^{h53}$, $R^{h54}$ or $R^{h55}$ may be different.

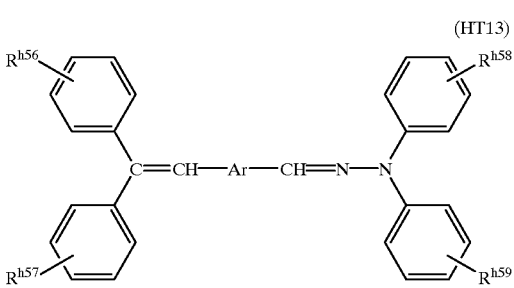
(HT13)

wherein $R^{h56}$, $R^{h57}$, $R^{h58}$ and $R^{h59}$ are the same or different and indicate a hydrogen atom, a halogen atom, an alkyl group or an alkoxy group; and Ar is a group (Ar1), (Ar2) or (Ar3) represented by the formula:

-continued (Ar3)

In the hole transferring material described above, examples of the alkyl group include the same groups as those described above. Examples of the alkoxy group include groups having 1 to 6 carbon atoms, such as methoxy, ethoxy, n-propoxy, isopropoxy, n-butoxy, isobutoxy, s-butoxy, t-butoxy, pentyloxy, hexyloxy, etc. Examples of the aryl group include phenyl, tolyl, xylyl, biphenyl, o-terphenyl, naphthyl, anthryl and phenanthryl. Examples of the halogen atom include fluorine, chlorine, bromine and iodine.

Examples of the substituent which may be substituted on the above group include halogen atom, amino group, hydroxyl group, optionally esterified carboxyl group, cyano group, alkyl group having 1 to 6 carbon atoms, alkoxy group having 1 to 6 carbon atoms, and alkenyl group having 2 to 6 carbon atoms which may have an aryl group. The position of the substituent to be substituted is not specifically limited.

In the present invention, in addition to the above hole transferring materials, there can be used hole transferring substances which have hitherto been known, such as nitrogen-containing cyclic compounds and condensed polycyclic compounds, e.g., oxadiazole compounds such as 2,5-di(4-methylaminophenyl)-1,3,4-oxadiazole; styryl compounds such as 9-(4-diethylaminostyryl)anthracene; carbazole compounds such as polyvinyl carbazole; organic polysilane compounds; pyrazoline compounds such as 1-phenyl- 3-(p-dimethylaminophenyl)pyrazoline; hydrazone compounds; triphenylamine compounds; indol compounds; oxazole compounds; isoxazole compounds, thiazole compounds; thiadiazole compounds; imidazole compounds; pyrazole compounds; and triazole compounds.

In the present invention, electron transferring materials are used alone or in any combination thereof. The binding resin is not required necessarily when using the electron transferring material having layer-forming properties, such as polyvinyl carbazole.

Among the above hole transferring materials, those having an ionization potential (Ip) of 4.8 to 5.6 eV are preferably used and those having a mobility of not less than $1 \times 10^{-6}$ cm$^2$/V second at an electric field strength of $3 \times 10^5$ V/cm are more preferred.

The residual potential is further lowered and the sensitivity is improved by using the hole transferring material having the ionization potential within the above range. The reason is not clear but considered as follows.

That is, an ease of injecting electric charges from the electric charge generating material into the hole transferring material has a close relation with the ionization potential of the hole transferring material. When the ionization potential of the hole transferring material is larger than the above range, the degree of injection of electric charges from the electric charge generating material into the hole transferring material becomes low, or the degree of the giving and receiving of holes between hole transferring materials becomes low, which results in deterioration of the sensitivity. On the other hand, in the system wherein the hole transferring material and electron transferring material coexist, it is necessary to pay attention to an interaction between them, more specifically formation of a charge transfer complex. When such a complex is formed between them, a recombination arises between holes and electrons, which results in deterioration of the mobility of electric charges on the whole. When the ionization potential of the hole transferring material is smaller than the above range, a tendency to form a complex between the hole transferring material and electron transferring material becomes large and a recombination between electrons and holes arises. Therefore, an apparent yield of quantums is lowered, which results in deterioration of the sensitivity Examples of the hole transferring material which can be suitably used in the present invention include the compounds represented by the formula (HT1-1):

(HT1-1)

which belong to the benzidine derivative represented by the above general formula (HT1).

In the present invention, by using the phenanthrylenediamine derivative represented by the above general formula (HT8) as the hole transferring material in combination with the above naphthoquinone derivative (1) as the electron transferring material, the sensitivity of the resulting photosensitive material and the stability of a surface potential when repeatedly forming an image are improved, and the wear resistance of the photosensitive material is also improved.

Examples of the phenanthrylenediamine derivative represented by the above general formula (HT8) include the following compounds:

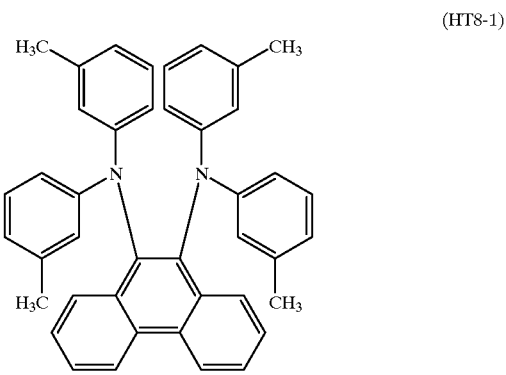

(HT8-1)

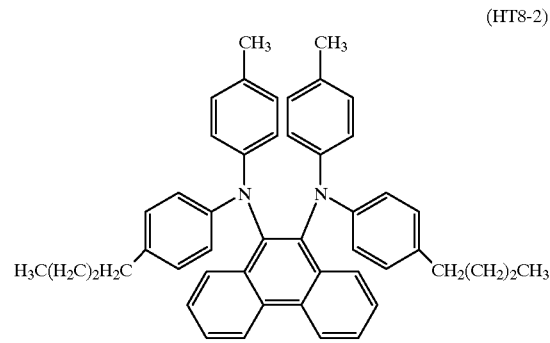

(HT8-2)

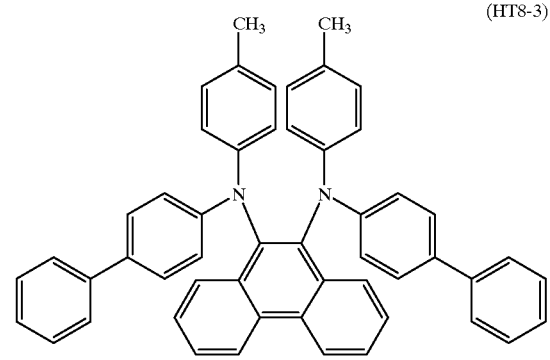

(HT8-3)

Electric Charge Generating Material

Examples of the electric charge generating material include compounds represented by the following formulas (CG1) to (CG12):

(CG1) Metal-free phthalocyanine

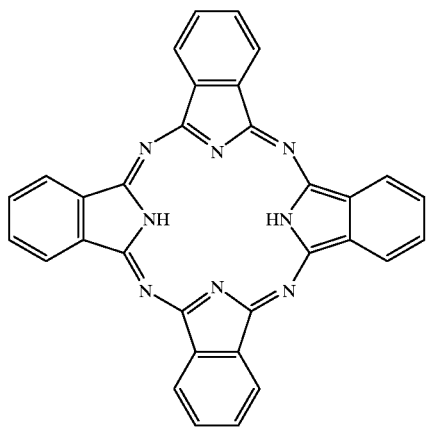

(CG1)

(CG2) Oxotitanyl phthalocyanine

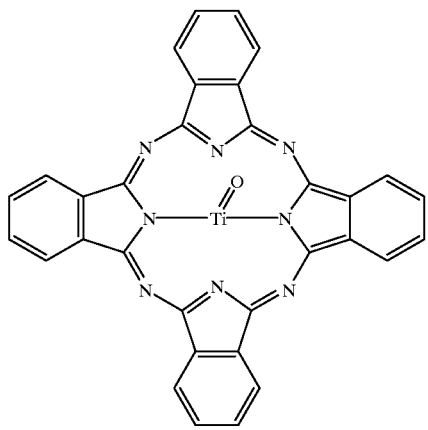

(CG2)

(CG3) Perylene pigment

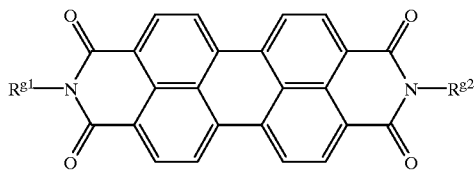

(CG3)

wherein $R^{g1}$ and $R^{g2}$ are the same or different and indicate a substituted or non-substituted alkyl group having not more than 18 carbon atoms, a cycloalkyl group, an aryl group, an alkanoyl group or an aralkyl group.

(CG4) Bisazo pigment

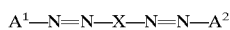  (CG4)

wherein $A^1$ and $A^2$ are the same or different and indicate a coupler residue; and X is

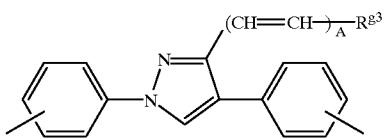

wherein $R^{g3}$ is a hydrogen atom, an alkyl group, an aryl group or a heterocyclic group, and the aryl group or heterocyclic group may have a substituent; and A is 0 or 1,

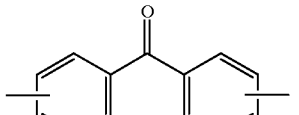

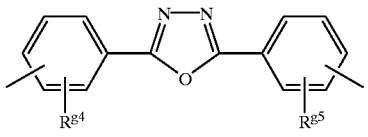

wherein $R^{g4}$ and $R^{g5}$ are the same or different and indicate a hydrogen atom, an alkyl group having 1 to 5 carbon atoms, a halogen atom, an alkoxy group, an aryl group or an aralkyl group,

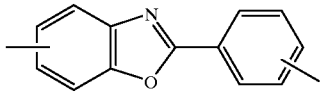

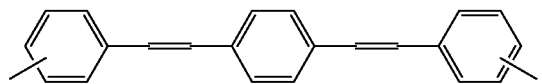

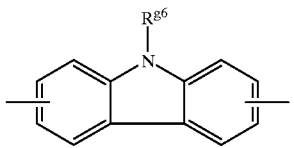

wherein $R^{g6}$ is a hydrogen atom, an ethyl group, a chloroethyl group or a hydroxyethyl group,

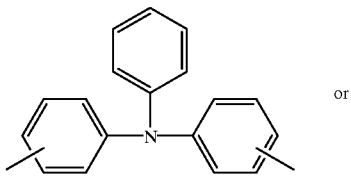

or

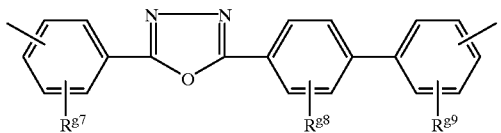

wherein $R^{g7}$, $R^{g8}$ and $R^{g9}$ are the same or different and indicate a hydrogen atom, an alkyl group having 1 to 5 carbon atoms, a halogen atom, an alkoxy group, an aryl group or an aralkyl group.

(CG5) Dithioketopyrrolopyrrole pigment

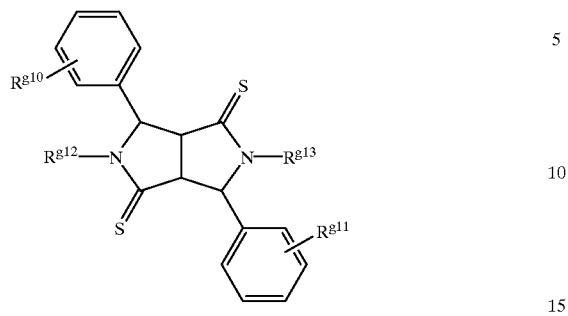

(CG5)

wherein $R^{g10}$ and $R^{g11}$ are the same or different and indicate a hydrogen atom, an alkyl group, an alkoxy group or a halogen atom; and $R^{g12}$ and $R^{g13}$ are the same or different and indicate a hydrogen atom, an alkyl group or an aryl group.

(CG6) Metal-free naphthalocyanine pigment

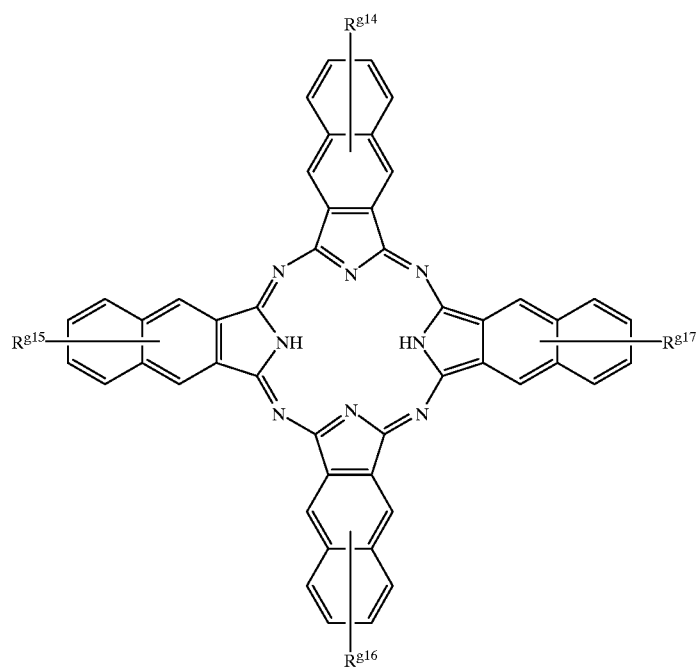

(CG6)

wherein $R^{g14}$, $R^{g15}$, $R^{g16}$ and $R^{g17}$ are the same or different and indicate a hydrogen atom, an alkyl group, an alkoxy group or a halogen atom.

(CG7) Metal naphthalocyanine pigment (CG7)

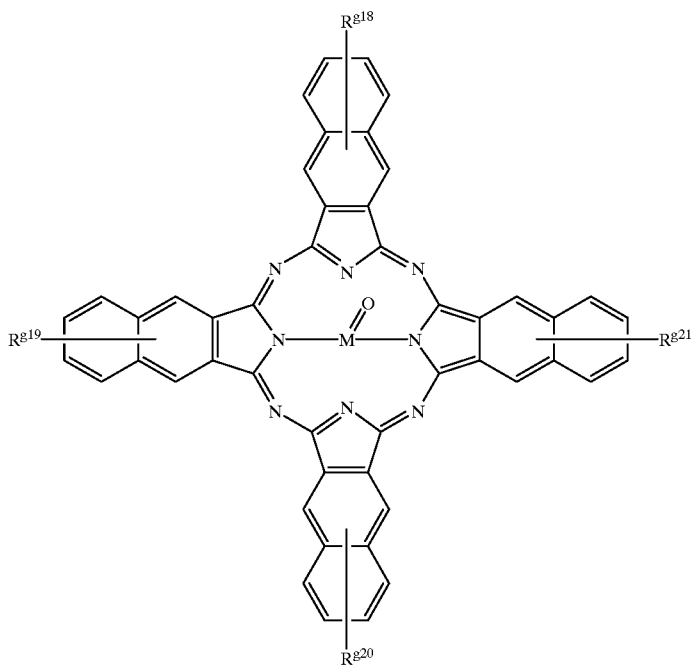

wherein $R^{g18}$, $R^{g19}$, $R^{g20}$ and $R^{g21}$ are the same or different and indicate a hydrogen atom, an alkyl group, an alkoxy group or a halogen atom; and M is Ti or V.

(CG8) Squaraine pigment

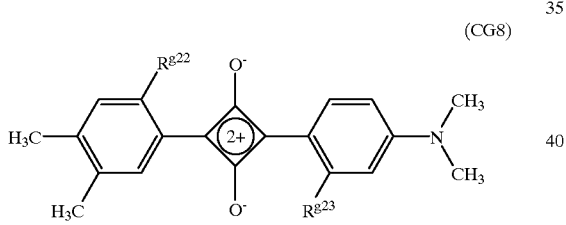

wherein $R^{g22}$ and $R^{g23}$ are the same or different and indicate a hydrogen atom, an alkyl group, an alkoxy group or a halogen atom.

(CG9) Trisazo pigment

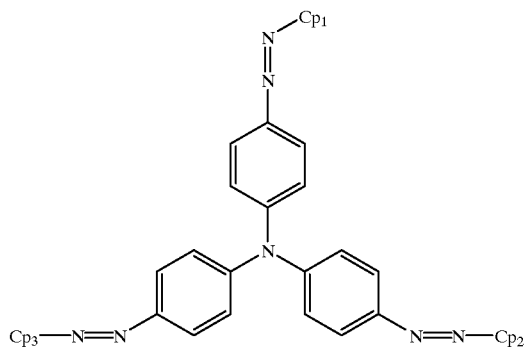

wherein $Cp_1$, $Cp_2$ and $Cp_3$ are the same or different and indicate a coupler residue.

(CG10) Indigo pigment

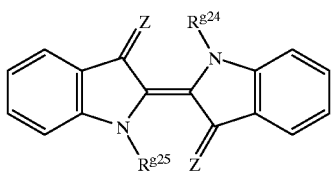

wherein $R^{g24}$ and $R^{g25}$ are the same or different and indicate a hydrogen atom, an alkyl group or an aryl group; and Z is an oxygen atom or a sulfur atom.

(CG11) Azulenium pigment

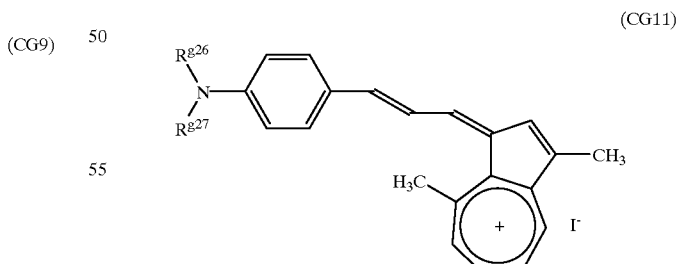

wherein $R^{g26}$ and $R^{g27}$ are the same or different and indicate a hydrogen atom, an alkyl group or an aryl group, and (CG12) Cyanine pigment (CG12)

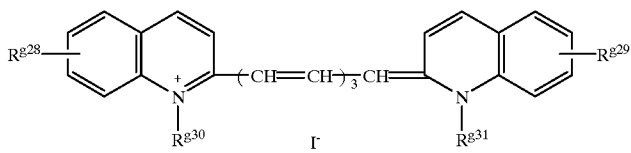

wherein $R^{g28}$ and $R^{g29}$ are the same or different and indicate a hydrogen atom, an alkyl group, an alkoxy group or a halogen atom; and $R^{g30}$ and $R^{g31}$ are the same or different and indicate a hydrogen atom, an alkyl group or an aryl group.

In the electric charge generating material described above, examples of the alkyl group include the same groups as those described above. The alkyl group having 1 to 5 carbon atoms include alkyl group having 1 to 6 carbon atoms except for the alkyl group having 6 carbon atoms. Examples of the substituted or non-substituted alkyl group having not more than 18 carbon atoms include heptyl, octyl, nonyl, decyl, dodecyl, tridecul, pentadecyl and octadecyl, in addition to the above-described alkyl group having 1 to 6 carbon atoms. Examples of the cycloalkyl group include groups having 3 to 8 carbon atoms, such as cyclopropyl, cyclobutyl, cyclopentyl, cyclohexyl, cycloheptyl and cyclooctyl. Examples of the alkoxy group, aryl group and aralkyl group include the same groups as those described above. Examples of the alkanoyl group include formyl, acetyl, propionyl, butylyl, pentanoyl and hexanoyl.

Examples of the heterocyclic group include thienyl group, pyrrolyl group, pyrrolidinyl group, oxazolyl group, isoxazolyl group, thiazolyl group, isothiazolyl group, imidazolyl group, 2H-imidazolyl group, pyrazolyl group, triazolyl group, tetrazolyl group, pyranyl group, pyridyl group, piperidyl group, piperidino group, 3-morpholinyl group, morpholino group and thiazolyl group. It may also be a heterocyclic group condensed with an aromatic ring.

Examples of the substituent which may be substituted on the above group include halogen atom, amino group, hydroxyl group, optionally esterified carboxyl group, cyano group, alkyl group having 1 to 6 carbon atoms, alkoxy group having 1 to 6 carbon atoms, alkenyl group having 2 to 6 carbon atoms which may have an aryl group, etc.

Examples of the coupler residue represented by $A^1$, $A^2$, $Cp_1$, $Cp_2$ and $Cp_3$ include groups shown in the following formulas (21) to (27):

(21)

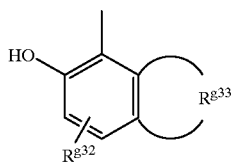

(22)

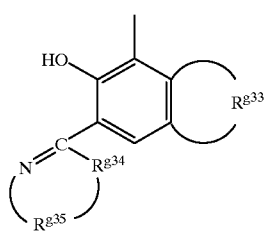

-continued (23)

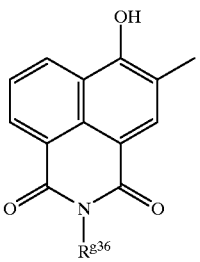

(24)

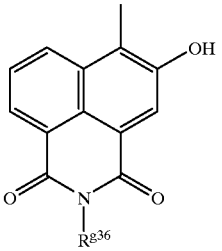

(25)

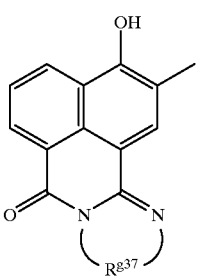

(26)

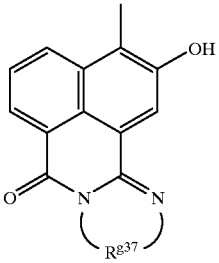

(27)

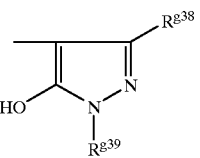

In the respective formulas, $R^{g32}$ is a carbamoyl group, a sulfamoyl group, an allophanoyl group, oxamoyl group, anthraninoyl group, carbazoyl group, glycyl group, hydantoyl group, phthalamoyl group or a succinamoyl group. These groups may have substituents such as halogen atom, phenyl group which may have a substituent, naphthyl group which may have a substituent, nitro group, cyano group, alkyl group, alkenyl group, carbonyl group or carboxyl group.

$R^{g33}$ is an atomic group which is required to form an aromatic ring, a polycyclic hydrocarbon or a heterocycle by condensing with a benzene ring, and these rings may have the same substituents as those described above.

$R^{g34}$ is an oxygen atom, a sulfur atom or an imino group.

$R^{g35}$ is a divalent chain hydrocarbon or aromatic hydrocarbon group, and these groups may have the same substituents as those described above.

$R^{g36}$ is an alkyl group, an aralkyl group, an aryl group or a heterocyclic group, and these groups may have the same substituents as those described above.

$R^{g37}$ is an atomic group which is required to form a heterocycle, together with a divalent chain hydrocarbon or aromatic hydrocarbon group or a moiety represented by the following formula (28):

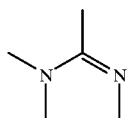

(28)

in the above general formulas (25) and (26), and these rings may have the same substituents as those described above.

$R^{g38}$ is a hydrogen atom, an alkyl group, an amino group, a carbamoyl group, a sulfamoyl group, an allophanoyl group, a carboxyl group, an alkoxycarbonyl group, an aryl group or a cyano group, and the groups other than a hydrogen atom may have the same substituents as those described above.

$R^{g39}$ is an alkyl group or an aryl group, and these groups may have the same substituent as those described above.

Examples of the alkenyl group include alkenyl groups having 2 to 6 carbon atoms, such as vinyl, allyl, 2-butenyl, 3-butenyl, 1-methylallyl, 2-pentenyl and 2-hexenyl.

In the above $R^{g33}$, examples of the atomic group which is required to form an aromatic ring by condensing with a benzene ring include alkylene groups having 1 to 4 carbon atoms, such as methylene, ethylene, propylene and butyrene.

Examples of the aromatic ring to be formed by condensing the above $R^{33}$ with a benzene ring include naphthalene ring, anthracene ring, phenanthrene ring, pyrene ring, chrysene ring and naphthacene ring.

In the above $R^{g33}$, examples of the atomic group which is required to form a polycyclic hydrocarbon by condensing with a benzene ring include alkylene groups having 1 to 4 carbon atoms, carbazole ring, benzocarbazole ring and dibenzofuran ring.

In the above $R^{g33}$, examples of the atomic group which is required to form a heterocycle by condensing with a benzene ring include benzofuranyl, benzothiophenyl, indolyl, 1H-indolyl, benzoxazoyl, benzothiazolyl, 1H-indadolyl, benzoimidazolyl, chromenyl, chromanyl, isochromanyl, quinolinyl, isoquinolinyl, cinnolinyl, phthalazinyl, quinazolinyl, quinoxalinyl, dibenzofranyl, carbazoyl, xanthenyl, acridinyl, phenanthridinyl, phenazinyl, phenoxazinyl and thianthrenyl.

Examples of the aromatic heterocyclic group to be formed by condensing the above $R^{g33}$ and the benzene ring include thienyl, furyl, pyrrolyl, oxazolyl, isoxazolyl, thiazolyl, isothiazl, imidazolyl, pyrazolyl, triazolyl, tetrazolyl, pyridyl and thiazolyl. In addition, it may also be a heterocyclic group condensed with the other aromatic ring (e.g. benzofuranyl, benzoimidazolyl, benzoxazolyl, benzothiazolyl, quinolyl).

In the above $R^{g35}$ and $R^{g37}$, examples of the divalent chain hydrocarbon include ethylene, propylene, butyrene, etc. Examples of the divalent aromatic hydrocarbon include phenylene, naphthylene and phenanthrilene.

In the above $R^{g36}$, examples of the heterocyclic group include pyridyl, pyrazyl, thienyl, pyranyl, indolyl, etc.

In the above $R^{g37}$, examples of the atomic group which is required to form a heterocycle, together with the moiety represented by the above formula (28), include phenylene, naphthylene, phenanthrilene, ethylene, propylene and butyrene.

Examples of the aromatic heterocyclic group to be formed by the above $R^{g37}$ and moiety represented by the above formula (28) include benzoimidazole, benzo[f]benzoimidazole, dibenzo[e,g]benzoimidazole and benzopyrimidine. These groups may have the same groups as those described above.

In the above $R^{g38}$, examples of the alkoxycarbonyl group include groups such as methoxycarbonyl, ethoxycarbonyl, propoxycarbonyl and butoxycarbonyl.

In the present invention, there can be used electric charge generating material which have hitherto been known, such as selenium, selenium-tellurium, amorphous silicon, pyrilium salt, anthanthrone pigments, triphenylmethane pigments, threne pigments, toluidine pigments, pyrazoline pigments and quinacridone pigments, in addition to the above electric charge generating materials.

The above electric charge generating materials can be used alone or in any combination thereof to present an absorption wavelength within a desired range. In that case, it is preferred to use, as the above electric charge generating material, those having the ionization potential which is balanced with that of the hole transferring material, in connection with the use of those having the ionization potential of 4.8 to 5.6 eV as the hole transferring material. Specifically, the above electric charge generating material preferably has an ionization potential of 4.8 to 6.0 eV, particularly 5.0 to 5.8 eV, in order to decrease the residual potential and to improve the sensitivity.

Examples of the most preferred electric charge generating material include phthalocyanine pigments such as X type metal-free phthalocyanine represented by the above general formula (CG1), oxotitanyl phthalocyanine represented by the general formula (CG2) and perylene pigments represented by the above general formulas (CG3).

Among the above perylene pigments, a compound represented by the general formula (CG3a):

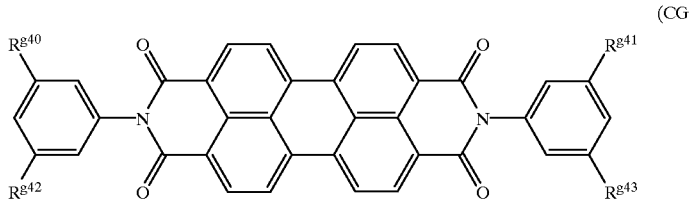

(CG3a)

wherein $R^{g40}$, $R^{g41}$, $R^{g42}$ and $R^{g43}$ are the same or different and indicate a hydrogen atom, an alkyl group, an alkoxy group or an aryl group, is suitably used. In the above general formula (CG3a), examples of the alkyl group, alkoxy group and aryl group, which correspond to the substituents $R^{g4}$ to $R^{g43}$, include the same groups as those described above.

Among the electric charge generating materials, the above phthalocyanine pigment is suitable as the electric charge generating material of the photosensitive material having a sensitivity at the wavelength range of not less than 700 nm. That is, the phthalocyanine pigment is superior in matching with the naphthoquinone derivative (electron transferring material) represented by the above general formula (1). Therefore, the electrophotosensitive material using both in combination of the present invention has a high sensitivity at the above wavelength range and it can be suitably used for a digital-optical image forming apparatus using a light source having a wavelength of not less than 700 nm.

The perylene pigment is suitable as the electric charge generating material of the photosensitive material having a sensitivity at the visible range. The perylene pigment (CG3a) is particularly superior in matching with the naphthoquinone derivative (electron transferring material) represented by the general formula (1). Therefore, the electrophotosensitive material using both in combination of the present invention has a high sensitivity at the visible range, so that it can be suitably used for an analog-optical image forming apparatus which employs a light source having a wavelength at the visible range.

Binding Resin

As a binding resin for dispersing the above respective components, there can be used various resins which have hitherto been used for the organic photosensitive material, and examples thereof include thermoplastic resins such as styrene polymer, styrene-butadiene copolymer, styrene-acrylonitrile copolymer, styrene-maleic acid copolymer, acrylic copolymer, styrene-acrylic acid copolymer, polyethylene, ethylene-vinyl acetate copolymer, chlorinated polyethylene, polyvinyl chloride, polypropylene, ionomer, vinyl chloride-vinyl acetate copolymer, polyester, alkyd resin, polyamide, polyurethane, polycarbonate, polyarylate, polysulfon, diaryl phthalate resin, ketone resin, polyvinyl butyral resin, polyether resin and polyester resin; crosslinking thermosetting resins such as silicone resin, epoxy resin, phenol resin, urea resin and melamine resin; photosetting resins such as epoxy acrylate and urethane acrylate. These binding resins can be used alone or in any combination thereof. Preferred resins are styrene polymer, acrylic polymer, styrene-acrylic copolymer, polyester, alkyd resin, polycarbonate and polyarylate.

A polyester resin, which is a substantially linear polymer, using at least one of a dihydroxy compound represented by the general formula (R1):

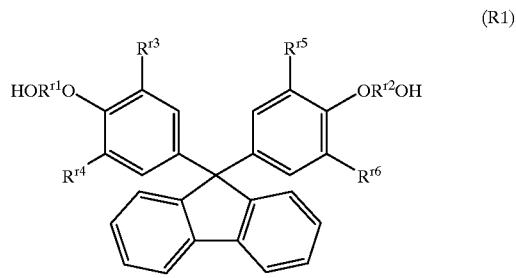

(R1)

wherein $R^{r1}$ and $R^{r2}$ are the same or different and indicate an alkylene group having 2 to 4 carbon atoms; and $R^{r3}$, $R^{r4}$, $R^{r5}$ and $R^{r6}$ are the same or different and indicate a hydrogen atom, an alkyl group having 1 to 4 carbon atoms, an aryl group or an aralkyl group, a dihydroxy compound represented by the general formula (R2):

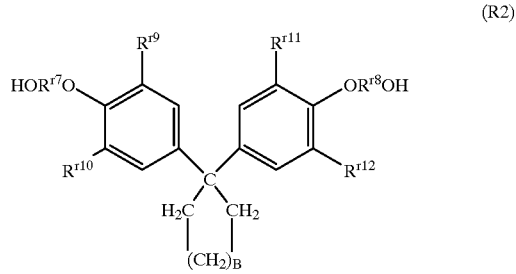

(R2)

wherein $R^{r7}$ and $R^{r8}$ are the same or different and indicate an alkylene group having 2 to 4 carbon atoms; $R^{r9}$, $R^{r10}$, $R^{r11}$ and $R^{r12}$ are the same or different and indicate a hydrogen atom, an alkyl group having 1 to 4 carbon atoms, an aryl group or an aralkyl group; and B is an integer of not less than 2, and a dihydroxy compound represented by the general formula (R3):

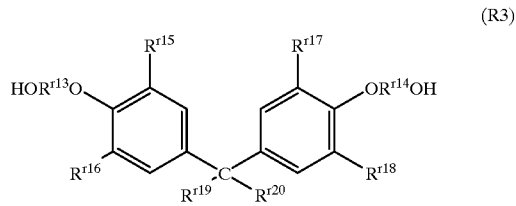

(R3)

wherein $R^{r13}$ and $R^{r14}$ are the same or different and indicate an alkylene group having 2 to 4 carbon atoms; $R^{r15}$, $R^{r16}$, $R^{r17}$ and $R^{r18}$ are the same or different and indicate a hydrogen atom, an alkyl group having 1 to 4 carbon atoms, an aryl group or an aralkyl group; and $R^{r19}$ and $R^{r20}$ are the same or different and indicate an alkyl group having 1 to 10 carbon atoms, is superior in adhesive properties with the conductive substrate and mechanical characteristics such as wear resistance and therefore, it is suitably used as the binding resin.

Specifically, the above polyester resin is a copolymer obtained by polycondensing a diol component containing at least one of the above three dihydroxy compounds with an acid component such as dicarboxylic acid or an ester forming derivative thereof. A proportion of the dihydroxy compound in the diol component is not less than 10 molar %, preferably not less than 30 molar %, more preferably not less than 50 molar %. When the proportion of the dihydroxy compound is less than 10 molar %, the heat resistance becomes insufficient and the photosensitive layer is liable to be deformed by heat. Also, the dispersion properties of the electric charge generating material and solubility in organic solvent are liable to be deteriorated.

It is preferred that the above polyester resin has an intrinsic viscosity (measured in chloroform at 20° C.) of not less than 0.3 dl/g, preferably not less than 0.4 dl/g. When the intrinsic viscosity is less than 0.3 dl/g, the mechanical characteristics of the photosensitive material, particularly wear resistance is deteriorated. On the other hand, when the intrinsic viscosity is more than 0.3 dl/g, a molded article having sufficient mechanical characteristics can be obtained. However, the larger the intrinsic viscosity, the longer the time required for dissolving the polyester resin in the solvent becomes. Therefore, the viscosity of the solution is liable to increase. When the viscosity of the solution is too high, it becomes difficult to apply a coating solution for forming the organic photosensitive layer on the conductive substrate. Therefore, when the intrinsic viscosity is not less than 2.5 dl/g, a problem on practical use arises. The polyester resin having an optimum intrinsic viscosity can be easily adjusted by controlling molecular weight adjustor, the melt polymerization conditions (e.g. polymerization time, polymerization temperature) and conditions of the chain propagation reaction of the post-step.

In the above general formulas (R1) to (R3) which indicate the dihydroxy compound, examples of the alkylene group having 2 to 4 carbon atoms, which corresponds to the groups $R^{r1}$, $R^{r2}$, $R^{r7}$, $R^{r8}$, $R^{r13}$ and $R^{r14}$, include ethylene, propylene and butylene.

Examples of the alkyl group having 1 to 4 carbon atoms, which corresponds to the groups $R^{r3}$ to $R^{r6}$, $R^{r9}$ to $R^{r12}$ and $R^{r15}$ to $R^{r18}$ include methyl, ethyl, normal propyl, isopropyl, normal butyl, isobutyl, secondary butyl, tertiary butyl, etc. Examples of the aryl group include phenyl, tolyl, xylyl, biphenyl, naphthyl, anthryl, phenanthryl, etc. Examples of the aralkl group include benzyl, benzhydryl, trityl and phenethyl.

In the general formula (R3), examples of the alkyl group having 1 to 10 carbon atoms, which corresponds to the groups $R^{r19}$ and $R^{r20}$ include the above alkyl group having 1 to 4 carbon atoms, pentyl, hexyl, heptyl, octyl, nonyl and decyl.

Among various dihydroxy compound, 9,9-bis[4-(2-hydroxyethoxy)phenyl]fluorene represented by the formula (R1-1) which belongs to the dihydroxy compound represented by the above general formula (R1) and 1,1-bis[4-(2-hydroxyethoxy)phenyl]-cyclohexane represented by the formula (R2-1) which belongs to the dihydroxy compounds represented by the above general formula (R2) are particularly preferred.

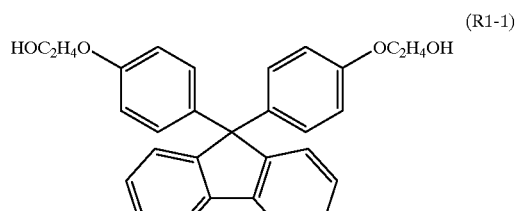

(R1-1)

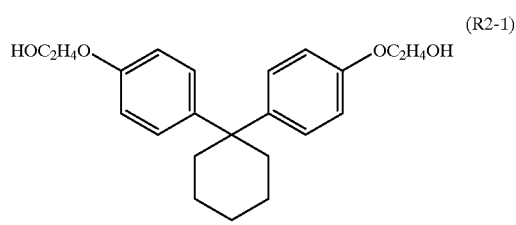

(R2-1)

Examples of the acid component constituting the polyester resin, together with the above dihydroxy compound, include aromatic dicarboxylic acids such as terephthalic acid, isophthalic acid, 1,2-naphthalenedicarboxylic acid, 1,3-naphthalenedicarboxylic acid, 1,4-naphthalenedicarboxylic acid, 1,5-naphthalenedicarboxylic acid, 1,6-naphthalenedicarboxylic acid, 1,7-naphthalenedicarboxylic acid, 1,8-naphthalenedicarboxylic acid, 2,3-naphthalenedicarboxylic acid, 2,6-naphthalenedicarboxylic acid, 2,7-naphthalenedicarboxylic acid, 2,2'-biphenyldicarboxylic acid, 3,3'-biphenyldicarboxylic acid, 4,4'-biphenyldicarboxylic acid, and 9,9-bis(4-carboxyphenylene)fluorene; aliphatic dicarboxylic acids such as maleic acid, adipic acid, sebacic acid and decamethylenedicarboxylic acid; and ester forming derivatives of these dicarboxylic acids. These may be used alone or in any combination thereof.

The most preferred acid components include dimethyl terephthalate represented by the formula (R4), 2,6-naphthalenedicarboxylic acid represented by the formula (R5) and terephthalic acid represented by the formula (R6).

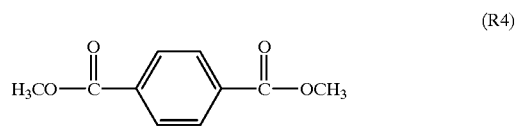

(R4)

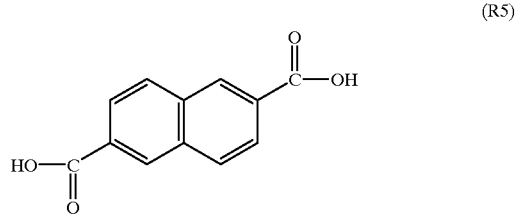

(R5)

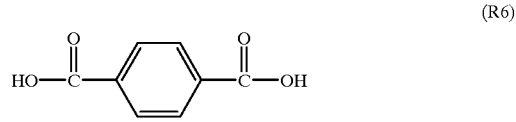

(R6)

As the other diol component, for example, there can be used aliphatic glycols such as ethylene glycol, 1,2-propanediol, 1,3-propanediol, 1,2-butanediol, 1,3-butanediol, 1,4-butanediol, 1,3-pentanediol, 1,4-pentanediol and 1,5-pentanediol; diols having an aromatic ring at the main chain or side chain, such as 1,1-bis[4-(2- hydroxyethoxy)phenyl]-1-phenylethane and 2,2-bis[4-(2-hydroxyethoxy)phenyl]-3-methylpentane; compounds having an aromatic ring and sulfur at the main chain, such as bis[4-(2-hydroxyethoxy)phenyl]sulfon; or other dihydroxy compounds, e.g., one or more tricyclodecanedimethylol.

Examples of the particularly preferred diol component include ethylene glycol represented by the formula (R7), 2,2-bis[4-(2-hydroxyethoxy)phenyl]-3-methylpentane represented by formula (R8), but are not limited thereto.

(R7)

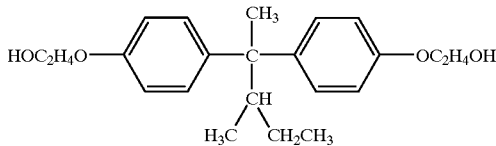

(R8)

In order to produce the polyester resin by polycondensing the above respective components, a suitable process may be selected from a known process utilized for the production of the conventional polyester resin, for example, melt polymerization method (e.g., transesterification process, direct polymerization process), solution polymerization process, and interfacial polymerization process. The reaction condition such as polymerization catalyst used for the production may be the same as that used in the production of the conventional polyester resin.

In order to produce the above polyester resin by the transesterification process among the melt polymerization process, the proportion of at least one dihydroxy compound selected from those represented by the general formulas (R1) to (R3) to the diol component in the resin is preferably 10 to 95 molar %. When the proportion of the diol component exceeds 95 molar %, there arose a problem that the melt polymerization reaction does not proceed and the polymerization time becomes drastically long. Even if the proportion is more than 95 molar %, the polyester resin can be easily produced by the solution polymerization process or interfacial polymerization process.

In the polyester resin (amorphous) obtained by copolymerizing the acid component with the diol component containing the dihydroxy compounds (R1) to (R3), the limit of the weight-average molecular weight (in polystyrene terms) which can be easily obtained by an already known polymerization process is 100,000 (intrinsic viscosity in chloroform: 2.5 dl/g).

In order to obtain the high-molecular polyester resin having the intrinsic viscosity of not less than 2.5 dl/g, the above components may be polymerized by the above process, followed by reacting with the diisocyanate. The molecular chain of the polyester resin is extended by this post-treatment and the intrinsic viscosity in chloroform can easily reach not less than 2.5 dl/g, thereby improving mechanical characteristics such as wear resistance.

Diisocyanate include all compounds wherein two isocyanate groups are present in the same molecule. Specific examples thereof include hexamethylene diisocyanate, 2,4-tolylene diisocyanate, 2,6-tolylene diisocyanate, methylene-4,4'-bisphenyl diisocyanate, xylylene diisocyanate, 3-isocyanate methyl-3,5,5,-trichlorocyclohexyl isocyanate, etc. These may be used alone or in combination thereof. Among these, methylene-4,4'-bisphenyl diisocyanate is particularly preferred.

An amount of the diisocyanate to be reacted with the polyester is normally within the range of 0.5-fold to 1.3-fold, preferably 0.8-fold to 1.1-fold, relative to the molar number of the polyester resin calculated on the basis of the number-average molecular weight. The terminal end of the polyester resin molecule is alcoholic OH group and the diisocyanate reacts with an alcohol to form an urethane bond, thereby accomplishing chain extension of the polyester resin. At this time, an amount (molar fraction) of the urethane bond introduced in the polyester resin normally become not more than 1% and, therefore, physical characteristics (e.g., refractive index, birefringence, glass transition point, transparency) of the whole resin are the same as those of the polyester before treatment.

A suitable catalyst may be optionally used in the above chain extension reaction. Preferred examples of the catalyst include metal catalyst (e.g., tin octylate, dibutyltin dilaurate, lead naphthenate), diazobiscyclo[2,2,2]octane and tri N-butylamine. An amount of the catalyst added varies depending on the temperature of the chain extension reaction, and the catalyst is normally added in an amount of not more than 0.01 mol, preferably not more than 0.001 mol, based on 1 mol of the diisocyanate.

The reaction proceeds by adding a suitable amount of the catalyst and diiosocyanate to the above polyester, followed by stirring under a dry nitrogen flow.

The reaction temperature of the chain extension reaction varies depending on the condition. When the reaction is conducted in an organic solvent, the reaction temperature is preferably set at the temperature lower than the boiling point of the solvent. When using no organic solvent, the reaction temperature is preferably set at the temperature higher than the glass transition temperature of the polyester resin. Since the obtainable molecular weight and coloring degree due to the secondary reaction are decided by the reaction temperature, the optimum reaction system and reaction temperature suitable for the system can be selected by taking the objective molecular weight and molecular weight of the polyester resin before reaction into consideration. For example, when using trichlorobenzene as the organic solvent, it becomes possible to conduct the reaction within the range of 130 to 150° C. and the coloring due to the secondary reaction hardly arise.

The molecular weight is drastically increased by the chain extension reaction of the above polyester resin and an increase in intrinsic viscosity is accomplished. The finally obtainable molecular weight varies depending on the molecular weight before reaction, but the molecular weight of the chain-extended polyester resin can be normally adjusted to the objective value by changing the reaction temperature, reaction time and amount of the diisocyanate. It is difficult to specify the reaction temperature and reaction time because it all depends. Normally, the higher the temperature the longer the reaction time, the higher the molecular weight becomes. When using the diisocyanate in an equal a mount to 1.1-fold amount relative to the molar number of the polyester resin calculated from the number-average molecular weight, the effect of chain extension is high.

The molecular weight of the polyester resin obtained by copolymerizing the acid component with the diol component containing the dihydroxy compounds (R1) to (R3) is about 20,000 (intrinsic viscosity: 0.5 dl/g) and is about 100,000 at most. For example, when the chain extension reaction is conducted using the polyester resin having the molecular weight of about 20,000, which can be most easily produced, as the raw material, a high-molecular weight polyester resin having the intrinsic viscosity of 0.7 to 1.5 dl/g can be obtained.

The molecular weight distribution of the chain-propagated polyester resin is generally wider. The molecular weight distribution of the amorphous polyester resin, which is obtained by copolymerizing the above special dihydroxy compound produced by the melt polymerization, varies depending on various conditions, and its ratio of the weight-average molecular weight to the number-average molecular weight is normally about 2. After the completion of the chain extension reaction, it normally become about 4 or more. In the case that the presence of the molecular weight distribution is not preferred, the molecular weight distribution can be controlled by optionally using a molecular weight fractionation method which has normally been known. As the molecular weight fractionation method, for example, there can be used reprecipitation method due to poor solvent, a method of passing through a column packed with a gel to sift according to the size of molecules, the method described in Analysis of polymers, T. R. Crompton, Pergamon Press, etc.

The above polyester resin may be used after mixing with the polycarbonate resin. Even when the polyester resin is used in combination with the material which is inferior in compatibility with the polyester resin, the compatibility can be improved by the polycarbonate resin.

The process for producing the electrophotosensitive material of the present invention will be described.

In order to obtain the single-layer electrophotosensitive material, a coating solution prepared by dissolving or dispersing a predetermined electron transferring material in a suitable solvent, together with an electric charge generating material, a hole transferring material and a binding resin, may be applied on a conductive substrate using means such as coating, followed by drying.

In the single-layer photosensitive material, the electric charge generating material is added in an amount of 0.1 to 50 parts by weight, preferably 0.5 to 30 parts by weight, based on 100 parts by weight of the binding resin. The electron transferring material is added in an amount of 5 to 100 parts by weight, preferably 10 to 80 parts by weight, based on 100 parts by weight of the binding resin. The hole transferring material is added in an amount of 5 to 500 parts by weight, preferably 25 to 200 parts by weight, based on 100 parts by weight of the binding resin. It is suitable that the total amount of the hole transferring material and electron transferring material is 20 to 500 parts by weight, preferably 30 to 200 parts by weight, based on 100 parts by weight of the binding resin. When containing the electron acceptive compound in the single-layer photosensitive layer, it is suitable to add the electron acceptive compound in an amount of 0.1 to 40 parts by weight, preferably 0.5 to 20 parts by weight, based on 100 parts by weight of the binding resin.

A thickness of the single-layer type photosensitive layer is 5 to 100 $\mu$m, preferably 10 to 50 $\mu$m.

In order to obtain the multi-layer photosensitive material, an electric charge generating layer containing an electric charge generating material may be formed on a conductive substrate using means such as depositing, coating, etc. and a coating solution containing an electron transferring material and a binding resin may be applied on this electric charge generating layer using means such as coating, followed by drying to form an electric charge transferring layer.

In the multi-layer photosensitive material, the electric charge generating material and binding resin, which constitute the electric charge generating layer, may be used in various proportions. It is suitable to add the electric charge generating material in an amount of 5 to 1000 parts by weight, preferably 30 to 500 parts by weight, based on 100 parts by weight of the binding resin. When containing the electron acceptive compound in the electric charge generating layer, it is suitable to add the electron acceptive compound in an amount of 0.1 to 40 parts by weight, preferably 0.5 to 20 parts by weight, based on 100 parts by weight of the binding resin. When containing the electron transferring material in the electric charge generating layer, it is suitable to add the electron transferring material in an amount of 0.5 to 50 parts by weight, preferably 1 to 40 parts by weight, based on 100 parts by weight of the binding resin.

The electron transferring material and binding resin, which constitute the electric charge transferring layer, can be used in various proportions within such a range as not to prevent transferring of electrons and to prevent the crystallization. It is suitable to add the electron transferring material in an amount of 10 to 500 parts by weight, preferably 25 to 100 parts by weight, based on 100 parts by weight of the binding resin to easily transfer electrons emitted by light irradiation in the electric charge generating layer. When containing the electron acceptive compound in the electric charge transferring layer, it is suitable to add the electron acceptive compound in an amount of 0.1 to 40 parts by weight, preferably 0.5 to 20 parts by weight, based on 100 parts by weight of the binding resin.

Regarding the thickness of the multi-layer photosensitive layer, a thickness of the electric charge generating layer is about 0.01 to 5 $\mu$m, preferably about 0.1 to 3 $\mu$m, and that of the electric charge transferring layer is 2 to 100 $\mu$m, preferably about 5 to 50 $\mu$m.

A barrier layer may be formed, in such a range as not to injure the characteristics of the photosensitive material, between the conductive substrate and photosensitive layer in the single-layer photosensitive material, or between the conductive substrate and electric charge generating layer, between the conductive substrate layer and electric charge transferring layer or between the electric charge generating layer and electric charge transferring layer in the multi-layer photosensitive material. A protective layer may be formed on the surface of the photosensitive layer.

Known various additives such as deterioration inhibitors (e.g., antioxidants, radical scavengers, singlet quenchers, ultraviolet absorbers), softeners, plasticizers, surface modifiers, bulking agents, thickening agents, dispersion stabilizers, wax, acceptors and donors can be added in various single-layer and multi-layer type photosensitive layers without injury to the electrophotographic characteristics.

In order to improve the sensitivity of the photosensitive layer, for example, known sensitizers such as terphenyl, halonaphthoquinones, acenaphthylene, etc. may be used in combination with the electric charge generating material.

Other electron transferring materials which have hitherto been known can be used in combination with the naphthoquinone derivative as the electron transferring material. Examples of the electron transferring material include various compounds having a high electron transferring capability, e.g. benzoquinone compound represented by the above general formula (2), diphenoquinone derivative represented by the general formula (3) and compounds represented by the following general formulas (ET1) to (ET12):

(ET1)

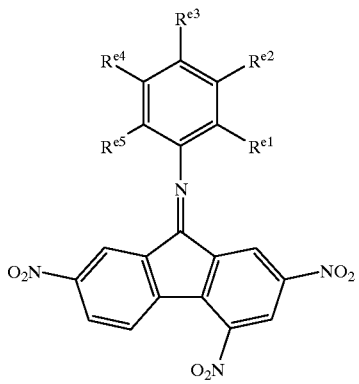

wherein $R^{e1}$, $R^{e2}$, $R^{e3}$, $R^{e4}$ and $R^{e5}$ are the same or different and indicate a hydrogen atom, an alkyl group which may have a substituent, an alkoxy group which may have a substituent, an aryl group which may have a substituent, an aralkyl group which may have a substituent, a phenoxy group which may have a substituent, or a halogen atom;

(ET2)

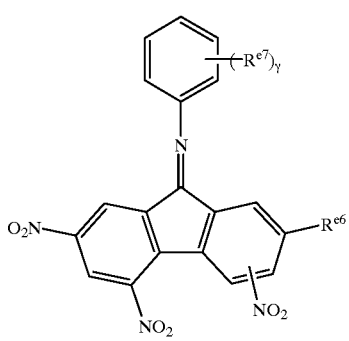

wherein $R^{e6}$ is an alkyl group; $R^{e7}$ is an alkyl group which may have a substituent, an alkoxy group which may have a substituent, an aryl group which may have a substituent, an aralkyl group which may have a substituent, a halogen atom or an alkyl halide group; and $\gamma$ is an integer of 0 to 5, provided that when $\gamma$ is not less than 2, each $R^{e7}$ may be different;

(ET3)

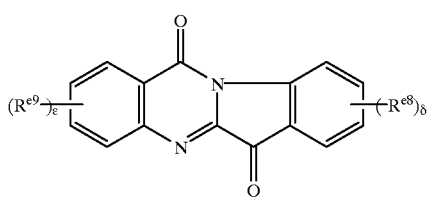

wherein $R^{e8}$ and $R^{e9}$ are the same or different and indicate an alkyl group; $\delta$ is an integer of 1 to 4; and $\epsilon$ is an integer of 0 to 4, provided that when $\delta$ and $\epsilon$ are not less than 2, plural groups represented by $R^{e8}$ or $R^{e9}$ may be different;

(ET4)

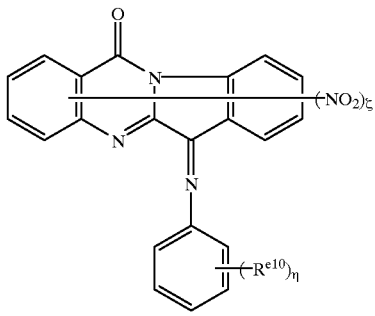

wherein $R^{e10}$ is an alkyl group, an aryl group, an aralkyl group, an alkoxy group, an alkyl halide group or a halogen atom; $\zeta$ is an integer of 0 to 4; and $\eta$ is an integer of 0 to 5, provided that when $\eta$ is not less than 2, each $R^{e10}$ may be different;

(ET5)

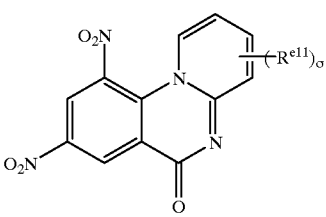

wherein $R^{e11}$ is an alkyl group; and $\sigma$ is an integer of 1 to 4, provided that when $\sigma$ is not less than 2, each $R^{e11}$ may be different;

(ET6)

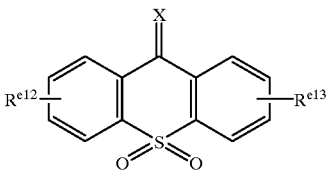

wherein $R^{e12}$ and $R^{e13}$ are the same or different and indicate a hydrogen atom, a halogen atom, an alkyl group, an aryl group, an aralkyloxycarbonyl group, an alkoxy group, a hydroxyl group, a nitro group or a cyano group; and X is a group of O, N—CN or $C(CN)_2$;

(ET7)

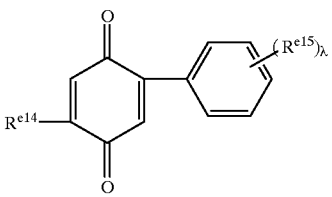

wherein $R^{e14}$ is a hydrogen atom, a halogen atom, an alkyl group, or a phenyl group which may have a substituent; $R^{e15}$ is a hydrogen atom, a halogen atom, an alkyl group which may have a substituent, a phenyl group which may have a substituent, an alkoxycarbonyl group, an N-alkylcarbamoyl group, a cyano group or a nitro group; and $\lambda$ is an integer of 1 to 3, provided that each $R^{e15}$ may be different when λ is not less than 2;

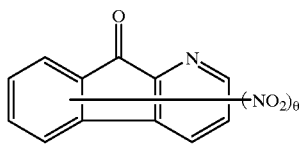
(ET8)

wherein θ is an integer of 1 to 2;

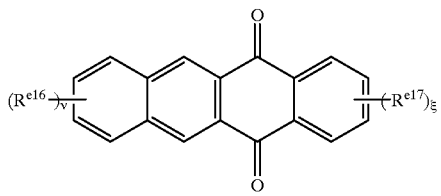
(ET9)

wherein $R^{e16}$ and $R^{e17}$ are the same or different and indicate a hydrogen atom, a halogen atom, an alkyl group which may have a substituent, a cyano group, a nitro group or an alkoxycarbonyl group; and ν and ξ indicate an integer of 1 to 3, provided that when ν and ξ are not less than 2, plural groups represented by $R^{e16}$ or $R^{e17}$ may be different;

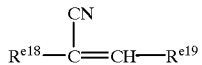
(ET10)

wherein $R^{e18}$ and $R^{e19}$ are the same or different and indicate a phenyl group, a polycyclic aromatic group or a heterocyclic group and these groups may have a substituent;

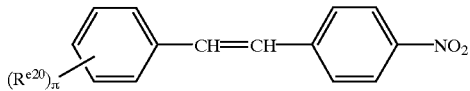
(ET11)

wherein $R^{e20}$ is an amino group, a dialkyl group, an alkoxy group, an alkyl group or a phenyl group; and π is an integer of 1 to 2, provided that each $R^{e2}$ may be different when π is 2; and

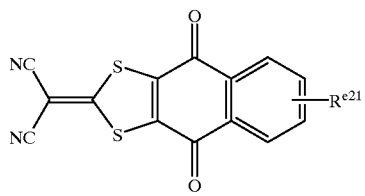
(ET12)

wherein $R^{e21}$ is a hydrogen atom, an alkyl group, an aryl group, an alkoxy group or an aralkyl group. Additional examples thereof include malononitrile, thiopyran compound, tetracyanoethylene, 2,4,8-trinitrothioxanthone, dinitrobenzene, dinitroanthracene, dinitroacridine, nitroanthraquinone, dinitroanthraquinone, succinic anhydride, maleic anhydride and dibromomaleic anhydride.

In the electron transferring material described above, examples of the alkyl group, alkoxy group, aryl group, aralkyl group and halogen atom include the same groups as those described above.

Examples of the alkyl halide group include alkyl halide group whose alkyl moiety having 1 to 6 carbon atoms, such as chloromethyl, bromomethyl, fluoromethyl, iodomethyl, 2-chloroethyl, 1-fluoroethyl, 3-chloropropyl, 2-bromopropyl, 1-chloropropyl, 2-chloro-1-methylethyl, 1-bromo-1-methylethyl, 4-iodobutyl, 3-fluorobutyl, 3-chloro-2-methylpropyl, 2-iodo-2-methylpropyl, 1-fluoro-2-methylpropyl, 2-chloro-1,1-dimethylethyl, 2-bromo-1,1-dimethylethyl, 5-bromopentyl and 4-chlorohexyl.

Examples of the polycyclic aromatic group include naphthyl, phenanthryl and anthryl.

Examples of the heterocyclic group include thienyl, pyrrolyl, pyrrolidinyl, oxazolyl, isoxazolyl, thiazolyl, isothiazolyl, imidazolyl, 2H-imidazolyl, pyrazolyl, triazolyl, tetrazolyl, pyranyl, pyridyl, piperidyl, piperidino, 3-morpholinyl, morpholino and thiazolyl. It may also be a heterocyclic group condensed with an aromatic ring.

Examples of the substituent which may be substituted on the above group include halogen atom, amino group, hydroxyl group, optionally esterified carboxyl group, cyano group, alkyl group having 1 to 6 carbon atoms, alkoxy group having 1 to 6 carbon atoms, and alkenyl group having 2 to 6 carbon atoms which may have an aryl group.

As the conductive substrate used for the photosensitive material of the present invention, various materials having a conductivity can be used, and examples thereof include metals such as aluminum, iron, copper, tin, platinum, silver, vanadium, molybdenum, chromium, cadmium, titanium, nickel, palladium, indium, stainless steel and brass; plastic materials on which the above metal is vapor-deposited or laminated; glass materials coated with aluminum iodide, tin oxide and indium oxide.

The conductive substrate may be made in the form of a sheet or a drum. The substrate itself may have a conductivity or only the surface of the substrate may have a conductivity. It is preferred that the conductive substrate has a sufficient mechanical strength when used.

The photosensitive layer in the present invention is produced by applying a coating solution, which is prepared by dissolving or dispersing a resin composition containing the above respective components in a solvent, on the conductive substrate, followed by drying.

That is, the above electric charge generating material, electric charge transferring material and binding resin may be dispersed may be mixed with a suitable solvent by a known method, for example, using a roll mill, a ball mill, an atriter, a paint shaker or a supersonic dispenser, to prepare a coating solution, followed by applying the solution and further drying.

As the solvent for preparing the coating solution, there can be used various organic solvents, and examples thereof include alcohols such as methanol, ethanol, isopropanol and butanol; aliphatic hydrocarbons such as n-hexane, octane and cyclohexane; aromatic hydrocarbons such as benzene, toluene and xylene; hydrocarbon halides such as dichloromethane, dichloroethane, carbon tetrachloride and chlorobenzene; ethers such as dimethyl ether, diethyl ether, tetrahydrofuran, ethylene glycol dimethyl ether and diethylene glycol dimethyl ether; ketones such as acetone, methyl ethyl ketone and cyclohexanone; esters such as ethyl acetate and methyl acetate; dimethylformaldehyde, dimethylformamide and dimethyl sulfoxide. These solvents may be used alone or in any combination thereof.

In order to improve a dispersibility of the electric charge transferring material and electric charge generating material as well as a smoothness of the surface of the photosensitive layer, there may be used surfactants, leveling agents and the like.

EXAMPLES

The following Examples and Comparative Examples further illustrate the present invention.

Synthesis of Naphthoquinone Derivative

Synthesis Example 1

Synthesis of 2-oxycarbonylethyl-3-phenyl-1,4-naphthoquinone

To a 500 ml two-necked flask connected with a reflux tube, 2-phenyl-1,3-indandione (41 g, 184 mmol) represented by the above general formula (1b) wherein $R^1$ is a phenyl group and sodium hydride (7.4 g, 60%, 185 mmol) using liquid paraffin as a protective medium were added. After the inside of the flask was sufficiently deaerated, dried and substituted with an argon gas, dehydrated tetrahydrofuran (250 ml) was added while ice-cooling the flask.

After ethyl bromoacetate (61 g, 368 mmol) represented by the above general formula (1c) wherein $R^3$ is an ethyl group was slowly added dropwise to the above solution, the solution was reacted under reflux with stirring for 5 hours.

The solution obtained after the completion of the reaction was added to an aqueous 1N hydrochloric acid solution (400 ml) to deposit a crystal, which was washed with water until the wash became neutral and then recrystallized from ethanol to synthesize ethyl-1,3-diketo-2-phenylindane-2-acetate (46.5 g, yield 82%) represented by the above general formula (1d) wherein $R^3$ is an ethyl group.

To a 500 ml two-necked flask connected with a reflux tube, the above 1,3-diketo-2-phenylindane-2-acetate (45 g, 146 mmol) and sodium hydride (5.9 g, 60%, 148 mmol) using liquid paraffin as a protective medium were added. After the inside of the flask was sufficiently deaerated, dried and substituted with an argon gas, dehydrated tetrahydrofuran (200 ml) was added while ice-cooling the flask.

After the above solution was reacted under reflux with stirring for 3 hours, the solution was added to an aqueous 1N hydrochloric acid solution (400 ml) to deposit a crystal, which was washed with water until the wash became neutral and then recrystallized from ethanol to synthesize 1,4-dihydroxy-2-oxycarbonylethyl-3-phenylnaphthalene represented by the above general formula (1e) wherein $R^3$ is an ethyl group (36 g, yield 80%).

To a 500 ml conical flask, the above 1,4-dihydroxy-2-oxycarbonylethyl-3-phenylnaphthalene (35 g, 114 mmol), silver oxide (26.4 g, 114 mmol) and chloroform (300 ml) were added and, after stirring at room temperature for 5 hours, the solid deposited in the solution was removed and the solution was concentrated to deposit a crystal.

This crystal was recrystallized from ethanol to produce the titled compound represented by the above general formula (10-1) (29.7 g, yield 85%).

The melting point of this product was 90° C. The infrared absorption spectrum of the product is shown in FIG. 2.

Synthesis Example 2

Synthesis of 2-oxycarbonylbenzyl-3-phenyl-1,4-naphthoquinone

According to the same manner as that described in Synthesis Example 1 except for using benzyl bromoacetate represented by the above general formula (1c) wherein $R^3$ is a benzyl group (84.3 g, 368 mmol), the titled compound represented by the above general formula (10-3) was produced (51.1 g, yield 75%).

Figure 3:
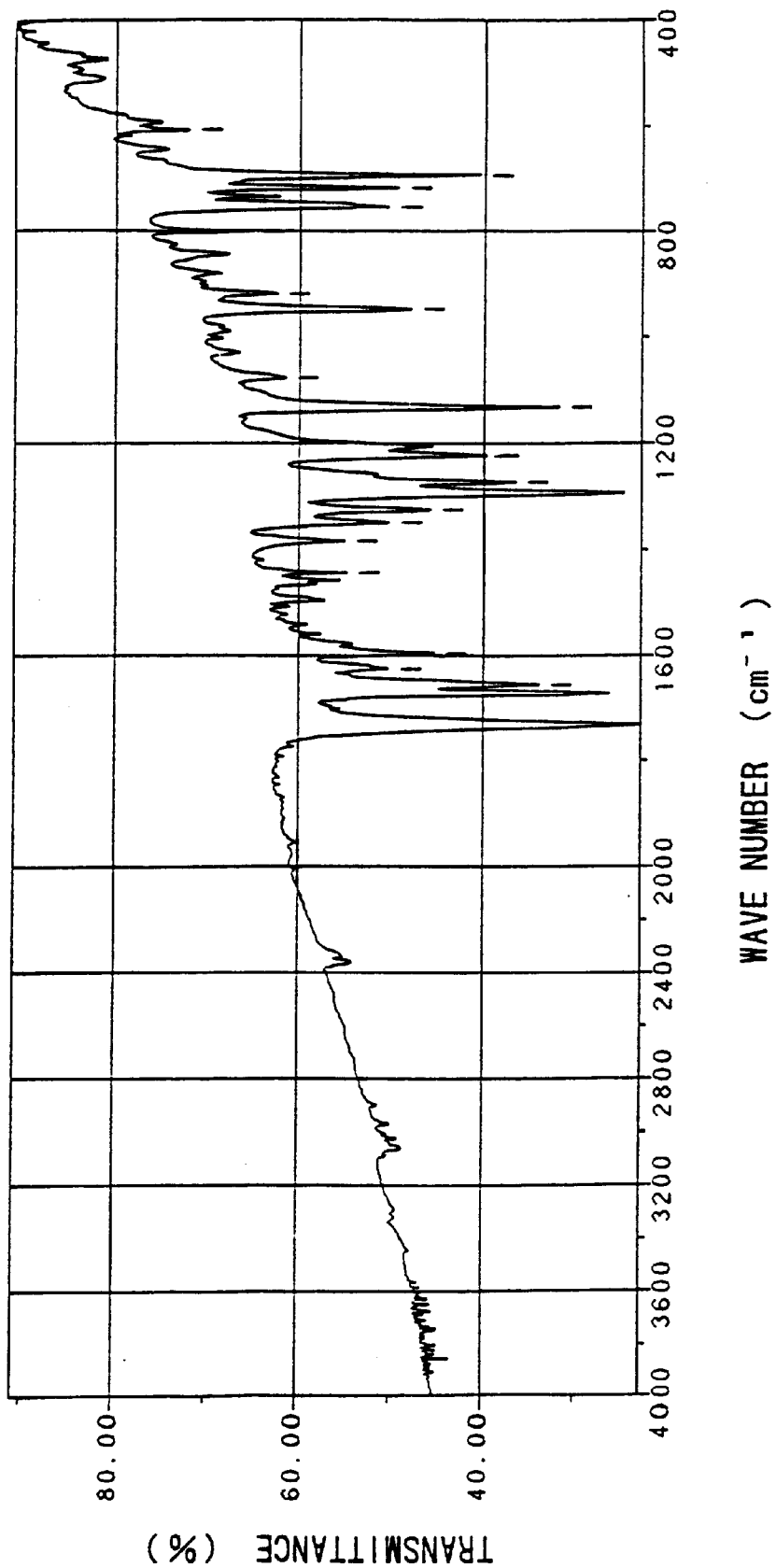
FIG. 3 is a graph illustrating an infrared absorption spectrum of the product synthesized in Synthetic Example 2.

The melting point of this product was 122 to 123° C. The infrared absorption spectrum of the product is shown in FIG. 3.

Synthesis Example 3

Synthesis of 3-methyl-2-oxycarbonylbenzyl-1,4-naphthoquinone

To a mixed solution of ethyl benzoate (50 g, 330 ml), ethyl propionate (23 g, 230 mmol) and cooled tetrahydrofuran (200 ml), sodium hydride (15.8 g, 395 mmol) was added with ice cooling and then the solution was reacted under reflux. During refluxing, the reaction was followed by thin-layer chromatography (TLC).

To the reaction solution obtained after the completion of the reaction, aqueous hydrochloric acid was added and the organic component was extracted with chloroform. The oil layer was separated and dried over sodium sulfate, and then the solvent was distilled off under reduced pressure to obtain a crude product.

Then, the crude product was purified by distilling off under reduced pressure under the condition of 103 to 107° C./5 mmHg to synthesize ethyl 2-benzoylpropionate (30.6 g, yield 65.2%) as a colorless liquid.

Concentrated sulfuric acid (260 g) was added to ethyl 2-benzoylpropionate (30.6 g, 149 mmol) and, after stirring at 85° C. for about 30 minutes, the reaction solution was added to ice. After the organic component was extracted with chloroform, the oil layer was separated and then dried over sodium sulfate. Then, the solvent was distilled off under reduced pressure. As a result, 2-methyl-1,3-indandione represented by the above general formula (1b) wherein $R^1$ is a methyl group (8.27 g, yield 35.0%) was obtained as a crystal containing an oil content.

Then, according to the same manner as that described in Synthesis Example 2 except for using 2-methyl-1,3-indandione (29.4 g, 184 mmol), the titled compound represented by the above general formula (10-4) was produced (23.6 g, yield 3.6%).

Figure 4:
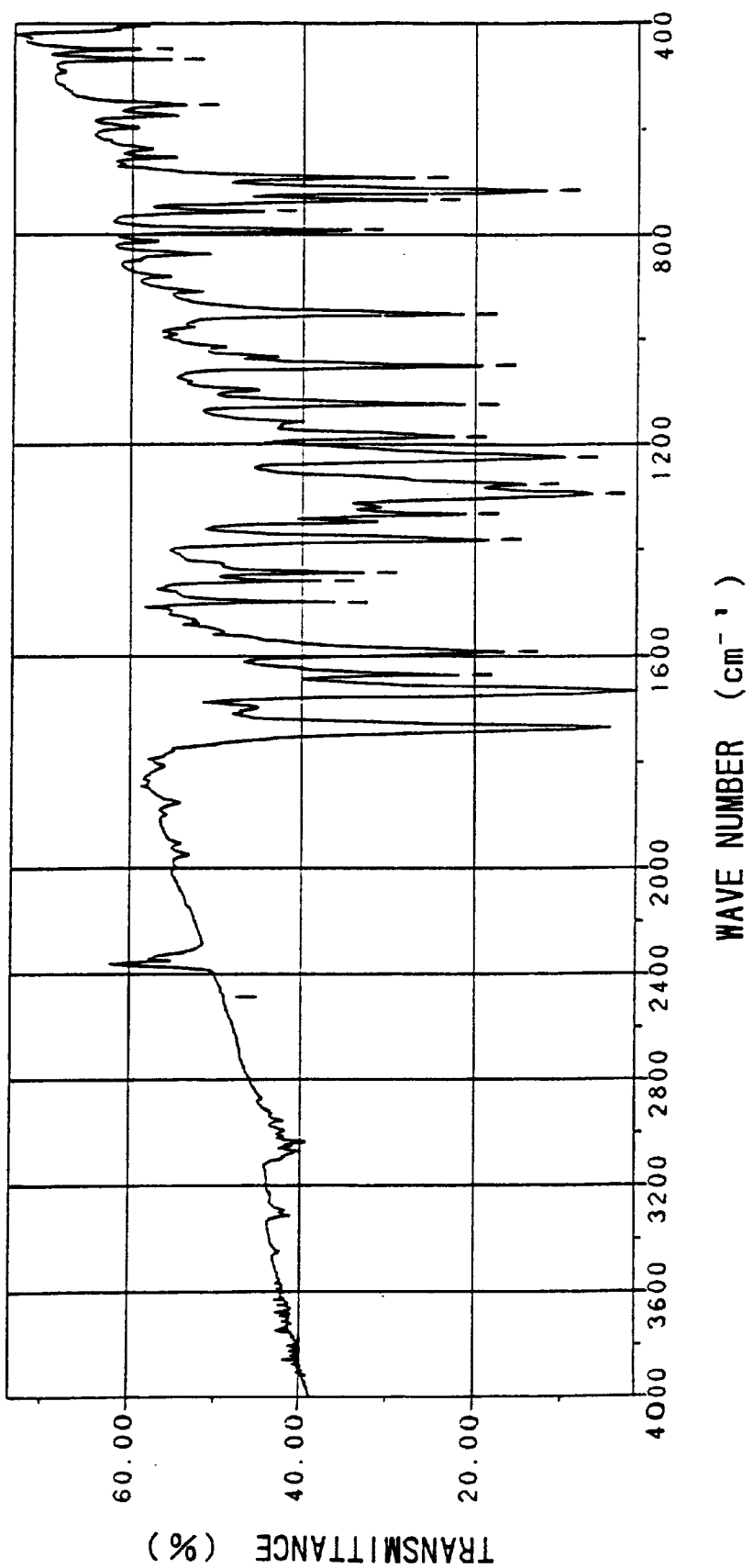
FIG. 4 is a graph illustrating an infrared absorption spectrum of the product synthesized in Synthetic Example 3.

The melting point of this product was 83 to 84° C. The infrared absorption spectrum of the product is shown in FIG. 4.

Synthesis Example 4

Synthesis of 2-(oxycarbonyl-4-methylphenyl)-3-phenyl-1,4-naphthoquinone

To a 500 ml two-necked flask, methylene chloride (200 ml), p-cresol (39.7 g, 367 mmol) and bromoacetic acid (51 g, 367 mmol) were added and, after slowly adding dropwise N,N'-dicyclohexylcarbodiimide (75.8 g, 367 mmol) with stirring under ice cooling, the solution was reacted with stirring at room temperature for 12 hours.

After the completion of the reaction, the solid deposited in the solution was removed and the solution was concentrated to obtain p-methylphenyl bromoacetate represented by the above general formula (1c) wherein $R^3$ is a p-methylphenyl group (83 g, yield 99%).

To a 500 ml two-necked flask connected with a reflux tube, 2-phenyl-1,3-indandione (41 g, 184 mmol) represented by the above general formula (1b) wherein $R^1$ is a phenyl group and sodium hydride (7.4 g, 60%, 185 mmol) using liquid paraffin as a protective medium were added. After the inside of the flask was sufficiently deaerated, dried and substituted with an argon gas, dehydrated tetrahydrofuran (250 ml) was added while ice-cooling the flask.

After p-methylphenyl bromoacetate (84.3 g, 368 mmol) represented was slowly added dropwise to the above solution, the solution was reacted under reflux with stirring for 5 hours.

After the completion of the reaction, the reaction solution was added to an aqueous 1N hydrochloric acid solution (400 ml) to deposit a crystal, which was washed with water until the wash became neutral and then recrystallized from ethanol to synthesize p-methylphenyl-1,3-diketo-2-phenylindane-2-acetate represented by the above general formula (1d) wherein $R^3$ is a p-methylphenyl group (56.5 g, yield 83%).

To a 500 ml two-necked flask connected with a reflux tube, the above p-methylphenyl-1,3-diketo-2-phenylindane-2-acetate (54 g, 146 mmol) and sodium hydride (5.9 g, 60%, 148 mmol) using liquid paraffin as a protective medium were added. After the inside of the flask was sufficiently deaerated, dried and substituted with an argon gas, dehydrated tetrahydrofuran (200 ml) was added while ice-cooling the flask.

After the above solution was reacted under reflux with stirring for 3 hours, the solution was added to an aqueous 1N hydrochloric acid solution (400 ml) to deposit a crystal, which was washed with water until the wash became neutral and then recrystallized from ethanol to synthesize 1,4-dihydroxy-2-(oxycarbonyl-4-methylphenyl)-3-phenylnaphthalene represented by the above general formula (1e) wherein $R^3$ is a p-methylphenyl group (42.7 g, yield 79%).

To a 500 ml conical flask, the above 1,4-dihydroxy-2-(oxycarbonyl-4-methylphenyl)-3-phenylnaphthalene (42 g, 114 mmol), silver oxide (26.4 g, 114 mmol) and chloroform (300 ml) were added and, after stirring at room temperature for 5 hours, the solid deposited in the solution was removed and the solution was concentrated to deposit a crystal.

This crystal was recrystallized from ethanol to produce the titled compound represented by the above general formula (10-5) (34.8 g, yield 83%).

Figure 5:
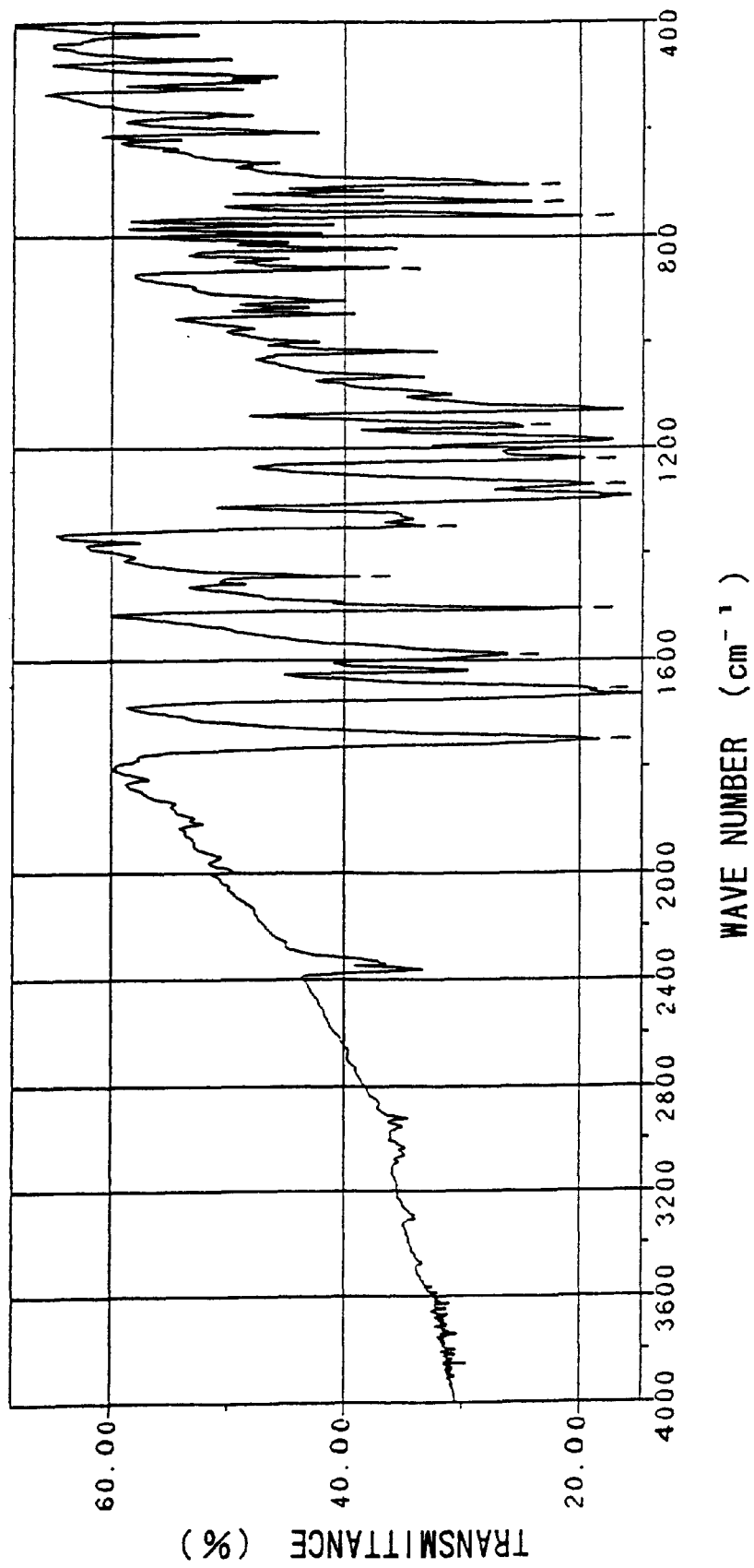
FIG. 5 is a graph illustrating an infrared absorption spectrum of the product synthesized in Synthetic Example 4.

The melting point of this product was 157° C. The infrared absorption spectrum of the product is shown in FIG. 5.

Synthesis Example 5
Synthesis of 2-(oxycarbonyl-4-ethylphenyl)-3-phenyl-1,4-naphthoquinone According to the same manner as that described in Synthesis Example 4 except for using p-ethylphenyl bromoacetate represented by the above general formula (1c) wherein $R^3$ is a p-ethylphenyl group (89.4 g, 368 mmol), the titled compound represented by the above general formula (10-7) was produced (49.7 g, yield 70%).

Figure 6:
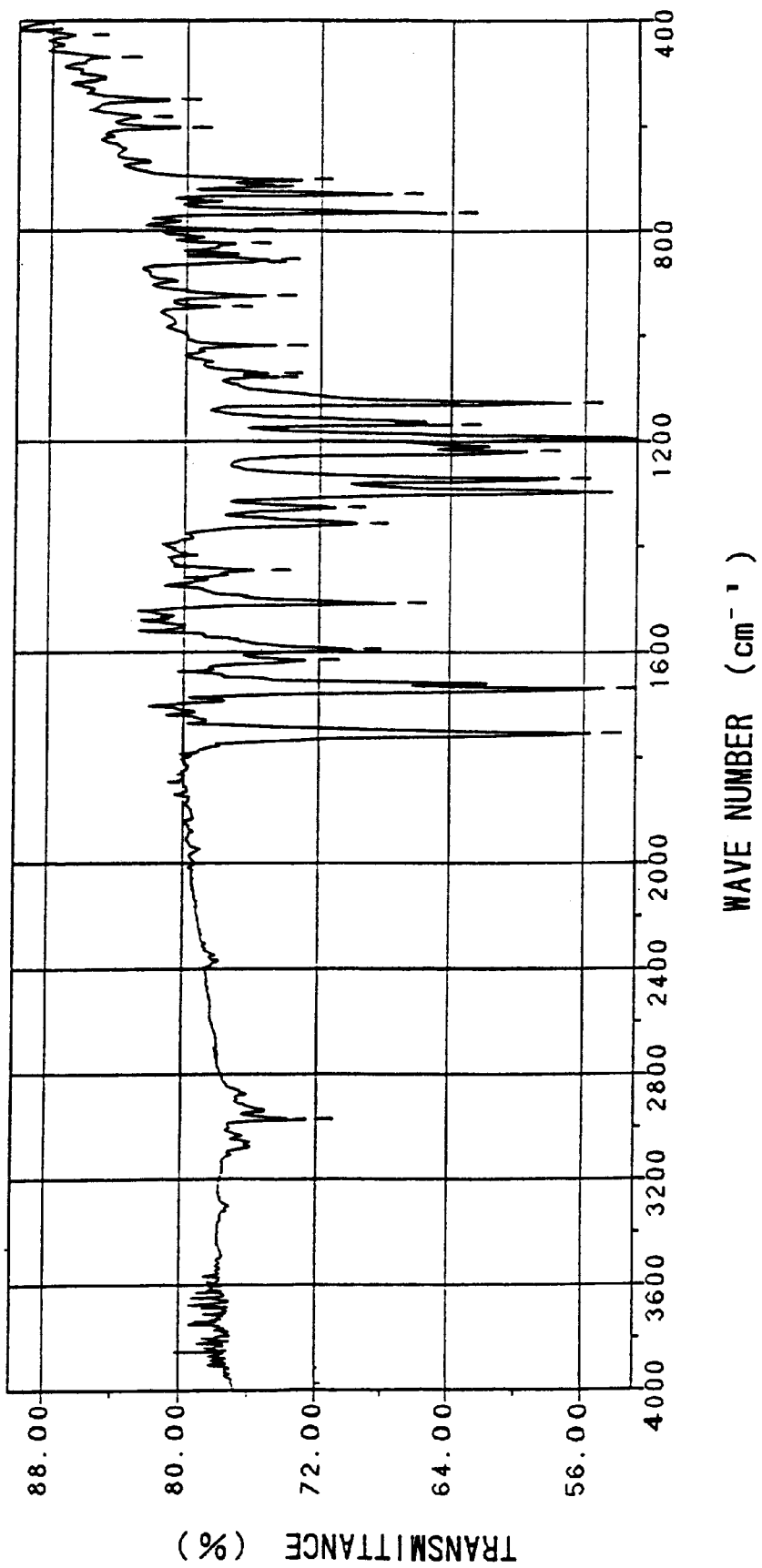
FIG. 6 is a graph illustrating an infrared absorption spectrum of the product synthesized in Synthetic Example 5.

The melting point of this product was 146 to 150° C. The infrared absorption spectrum of the product is shown in FIG. 6.

Synthesis Example 6
Synthesis of 2-benzoyl-3-phenyl-1,4-naphthoquinone

To a 500 ml two-necked flask connected with a reflux tube, 2-phenyl-1,3-indandione (41 g, 184 mmol) represented by the above general formula (1b) wherein $R^1$ is a phenyl group and sodium hydride (7.4 g, 60%, 185 mmol) using liquid paraffin as a protective medium were added. After the inside of the flask was sufficiently deaerated, dried and substituted with an argon gas, dehydrated tetrahydrofuran (250 ml) was added while ice-cooling the flask.

After phenacyl bromide represented by the above general formula (1f) wherein $R^2$ is a phenyl group (73.3 g, 368 mmol) was slowly added dropwise to the above solution, the solution was reacted under reflux with stirring for 5 hours.

After the completion of the reaction, the reaction solution was added to an aqueous 1N hydrochloric acid solution (400 ml) to deposit a crystal, which was washed with water until the wash became neutral and then recrystallized from ethanol to synthesize 1,3-diketo-2-benzoyl-2-phenylindane represented by the above general formula (1g) wherein $R^2$ is a phenyl group (50.7 g, yield 81%).

To a 500 ml two-necked flask connected with a reflux tube, the above 1,3-diketo-2-benzoyl-2-phenylindane (49.6 g, 146 mmol) and sodium hydride (5.9 g, 60%, 148 mmol) using liquid paraffin as a protective medium were added. After the inside of the flask was sufficiently deaerated, dried and substituted with an argon gas, dehydrated tetrahydrofuran (200 ml) was added while ice-cooling the flask.

After the above solution was reacted under reflux with stirring for 3 hours, the solution was added to an aqueous 1N hydrochloric acid solution (400 ml) to deposit a crystal, which was washed with water until the wash became neutral and then recrystallized from ethanol to synthesize 2-benzoyl-1,4-dihydroxy-3-phenylnaphthalene represented by the above general formula (1h) wherein $R^2$ is a phenyl group (36 g, yield 80%).

To a 500 ml conical flask, the above 2-benzoyl-1,4-dihydroxy-3-phenylnaphthalene (35 g, 103 mmol), silver oxide (23.8 g, 103 mmol) and chloroform (300 ml) were added and, after stirring at room temperature for 5 hours, the solid deposited in the solution was removed and the solution was concentrated to deposit a crystal.

This crystal was recrystallized from ethanol to produce the titled compound represented by the above general formula (1-1) (29.6 g, yield 85%).

Figure 7:
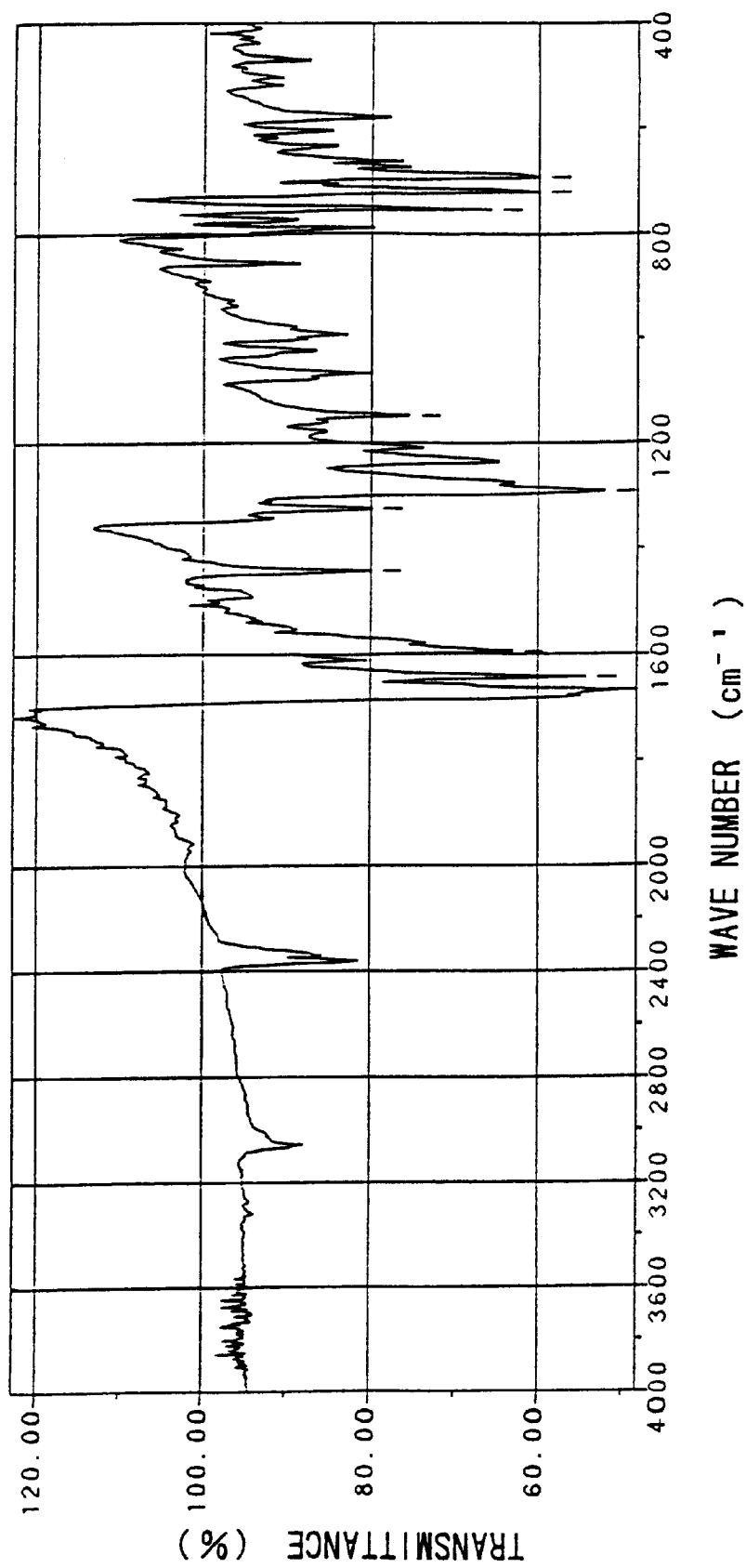
FIG. 7 is a graph illustrating an infrared absorption spectrum of the product synthesized in Synthetic Example 6.

The melting point of this product was 182° C. The infrared absorption spectrum of the product is shown in FIG. 7.

Synthesis Example 7
Synthesis of 2-benzoyl-3-(4-isopropylphenyl)-1,4-naphthoquinone According to the same manner as that described in Synthesis Example 6 except for using 2-(4-isopropylphenyl)-1,3-indandione represented by the above general formula (1b) wherein $R^1$ is an isopropylphenyl group (48.6 g, 184 mmol), the titled compound represented by the above general formula (1-3) was produced (36.2 g, yield 71.3%).

Figure 8:
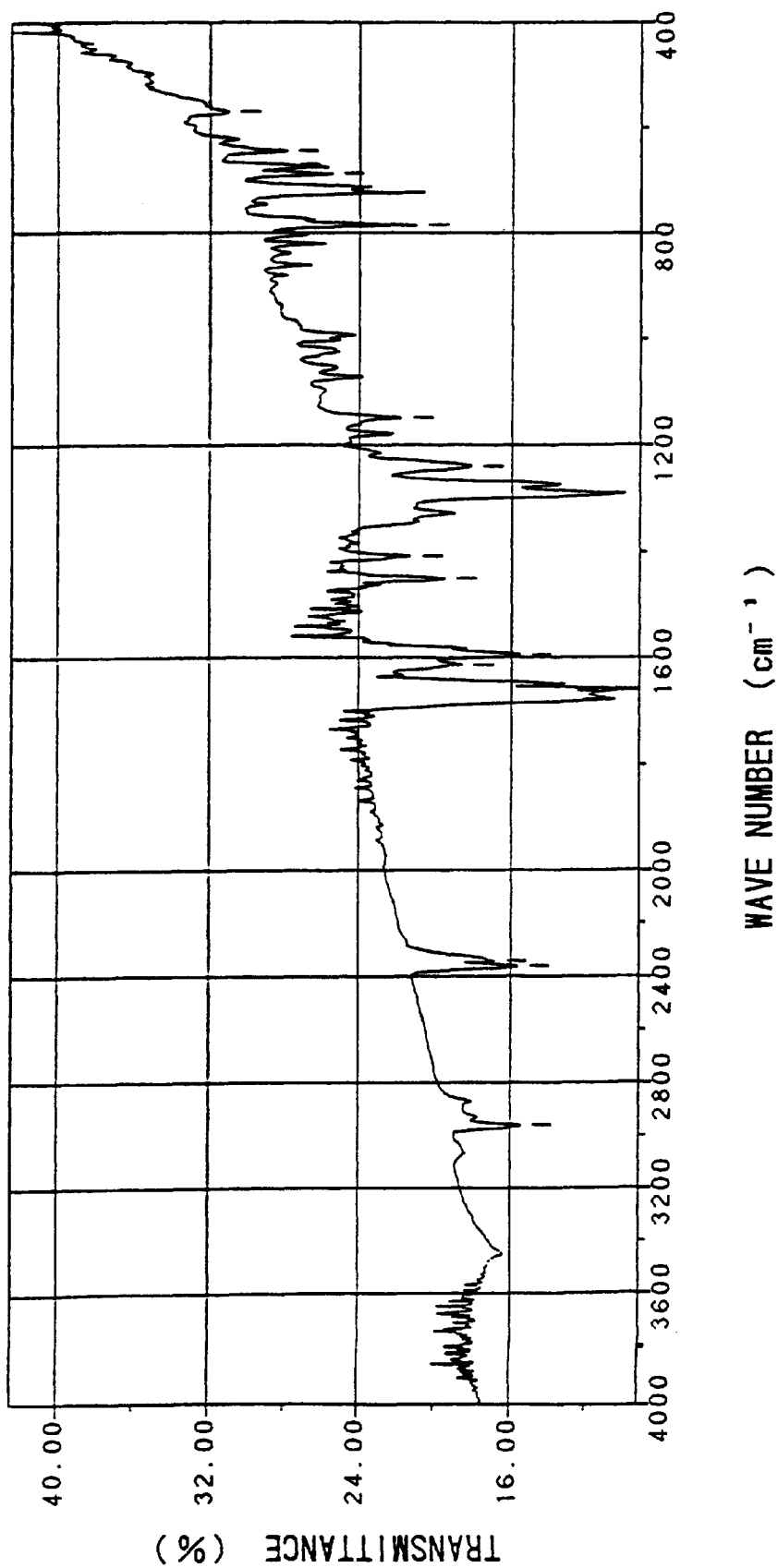
FIG. 8 is a graph illustrating an infrared absorption spectrum of the product synthesized in Synthetic Example 7.

The melting point of this product was 153 to 156° C. The infrared absorption spectrum of the product is shown in FIG. 8.

Synthesis Example 8
Synthesis of 2-benzoyl-3-methyl-1,4-naphthoquinone

According to the same manner as that described in Synthesis Example 6 except for using 2-methyl-1,3-indandione represented by the above general formula (1b) wherein $R^1$ is a methyl group (29.4 g, 184 mmol), the titled compound represented by the above general formula (1-4) was produced (34.6 g, yield 68.2%).

Figure 9:
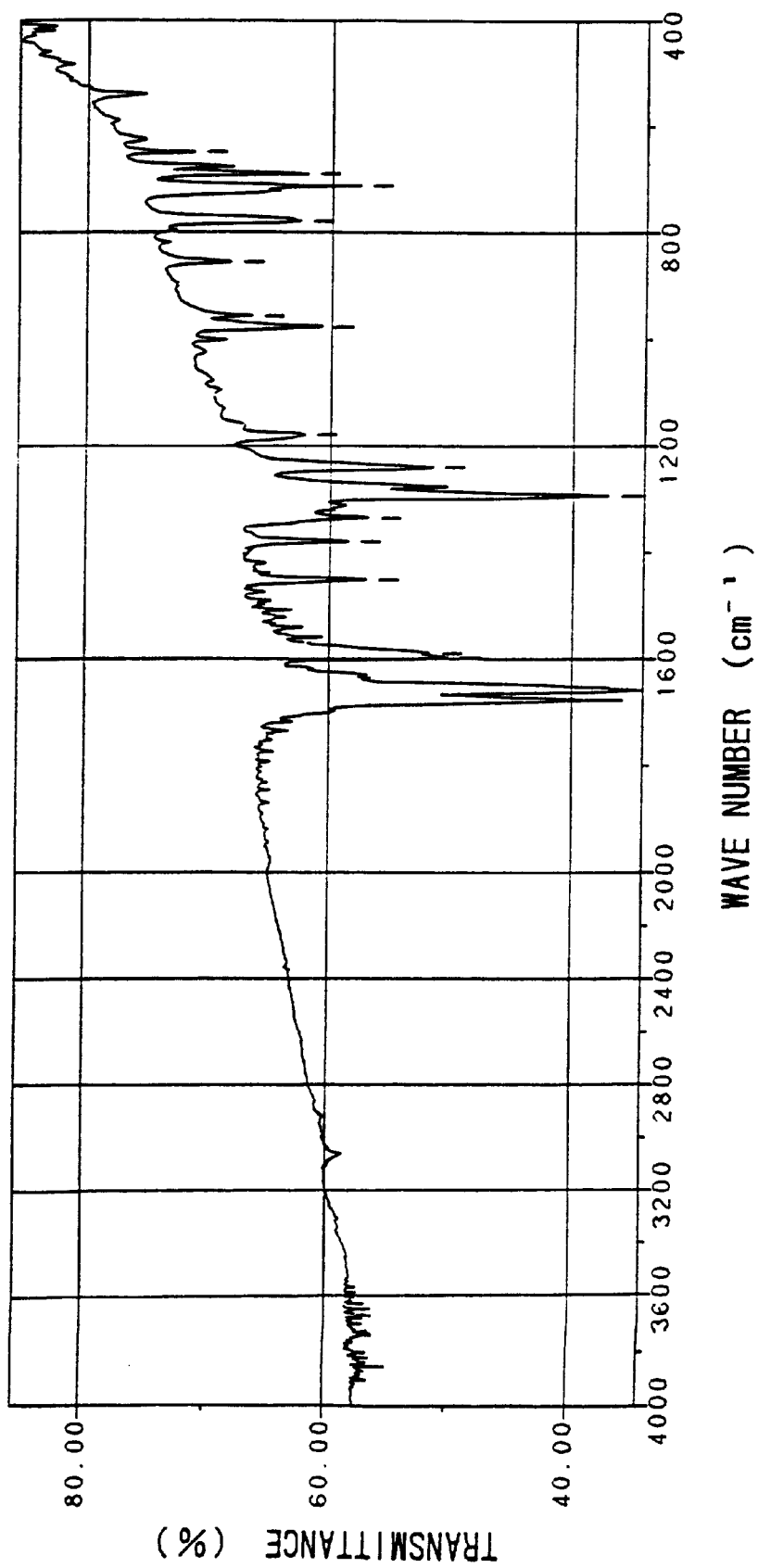
FIG. 9 is a graph illustrating an infrared absorption spectrum of the product synthesized in Synthetic Example 8.

The melting point of this product was 148 to 149° C. The infrared absorption spectrum of the product is shown in FIG. 9.

Photosensitive Material for Digital Light Source
(single-layer type)

Example 1

5 Parts by weight of X-type phthalocyanine (Ip=5.38 eV) represented by the above general formula (CG1) as the charge generating material (hereinafter referred to as "CGM"), 30 parts by weight of 2-oxycarbonylethyl-3-phenyl-1,4-naphthoquinone represented by the above general formula (10-1) obtained in Synthesis Example 1 as the electron transferring material (hereinafter referred to as "ETM"), 50 parts by weight of N,N,N',N'-tetrakis(p-methylphenyl)-3,3'-dimethylbenzidine (Ip=5.56 eV) represented by the above general formula (HT1-1) as the hole transferring material (hereinafter referred to as "HTM"), 100 parts by weight of polycarbonate as the binding resin and 800 parts by weight of tetrahydrofuran were mixed and dispersed in a ball mill for 50 hours to prepare a coating solution for single-layer type photosensitive layer.

The resulting coating solution was applied on an aluminum tube as the conductive substrate by a dip coating method, followed by hot-air drying at 100° C. for 60 minutes to form a single-layer type photosensitive layer having a thickness of 15 to 20 μm, thereby producing a photosensitive material for digital light source.

Example 2

According to the same manner as that described in Example 1 except that 5 parts by weight of oxotitanyl phthalocyanine (Ip=5.32 eV) represented by the above general formula (CG2) was used in place of X type metal-free phthalocyanine as the charge generating material (CGM), a photosensitive material for digital light source which has a single-layer type photosensitive layer was produced.

Examples 3 and 4

According to the same manner as that described in Examples 1 and 2 except that 30 parts by weight of 2-oxycarbonyl-t-butyl-3-phenyl-1,4-naphthoquinone represented by the above general formula (10-2) was used in place of 2-oxycarbonylethyl-3-phenyl-1,4-naphthoquinone as the electron transferring material, a photosensitive material for digital light source which has a single-layer type photosensitive layer was produced, respectively.

Examples 5 and 6

According to the same manner as that described in Examples 1 and 2 except that 30 parts by weight of 2-oxycarbonylbenzyl-3-phenyl-1,4-naphthoquinone represented by the above general formula (10-3) obtained in Synthesis Example 2 was used in place of 2-oxycarbonylethyl-3-phenyl-1,4-naphthoquinone as the electron transferring material, a photosensitive material for digital light source which has a single-layer type photosensitive layer was produced, respectively.

Examples 7 and 8

According to the same manner as that described in Examples 1 and 2 except that 30 parts by weight of 3-methyl-2-oxycarbonylbenzyl-1,4-naphthoquinone represented by the above general formula (10-4) obtained in Synthesis Example 3 was used in place of 2-oxycarbonylethyl-3-phenyl-1,4-naphthoquinone as the electron transferring material, a photosensitive material for digital light source which has a single-layer type photosensitive layer was produced, respectively.

Comparative Examples 1 and 2

According to the same manner as that described in Examples 1 and 2 except that 30 parts by weight of 3,5-dimethyl-3',5'-di-t-butyl-4,4'-diphenoquinone represented by the above general formula (3-1) was used in place of 2-oxycarbonylethylenyl-1,4-naphthoquinone as the electron transferring material, a photosensitive material for digital light source which has a single-layer type photosensitive layer was produced, respectively.

Comparative Examples 3 and 4

According to the same manner as that described in Examples 1 and 2 except for using 30 parts by weight of 3-phenyl-1,4-naphthoquinone represented by the formula (ET13):

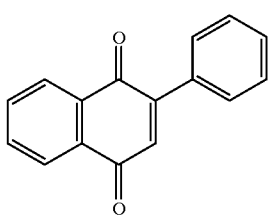

(ET13)

disclosed in the Japanese Laid-Open Patent Publication No. 6-110227 in place of 2-oxycarbonylmethyl-3-phenyl-1,4-naphthoquinone as the electron transferring material, a photosensitive material for digital light source which has a single-layer type photosensitive layer was produced, respectively.

Comparative Example 5

According to the same manner as that described in Example 1 except for containing no electron transferring material, an electrophotosensitive material for digital light source which has a single-layer type photosensitive layer was produced.

The electrophotosensitive materials of the above respective Examples and Comparative Examples were subjected to the following photosensitivity test I to evaluate their characteristics.

Photosensitivity Test I

By using a drum sensitivity tester manufactured by GENTEC Co., a voltage was applied on the surface of the electrophotosensitive material of the respective Examples and Comparative Examples to charge the surface at +700 V.

Then, monochromic light having a wavelength of 780 nm (half-width: 20 nm) and a light intensity of 16 μW/cm$^2$ from white light of a halogen lamp as an exposure light source of the above tester through a band-pass filter was irradiated on the surface of the photosensitive material (irradiation time: 80 msec.). Further, a surface potential at the time at which 330 msec. has passed since the beginning of exposure was measured as a potential after exposure VL (V). The smaller the potential after exposure VL (V), the higher the sensitivity of the photosensitive material is.

The results are shown in Table 1.

TABLE 1

| | CGM | ETM | HTM | VL (V) |
|---|---|---|---|---|
| EXAMPLE 1 | CG1 | 10-1 | HT1-1 | 178 |
| EXAMPLE 2 | CG2 | 10-1 | HT1-1 | 195 |
| EXAMPLE 3 | CG1 | 10-2 | HT1-1 | 180 |
| EXAMPLE 4 | CG2 | 10-2 | HT1-1 | 197 |
| EXAMPLE 5 | CG1 | 10-3 | HT1-1 | 170 |
| EXAMPLE 6 | CG2 | 10-3 | HT1-1 | 186 |
| EXAMPLE 7 | CG1 | 10-4 | HT1-1 | 170 |
| EXAMPLE 8 | CG2 | 10-4 | HT1-1 | 188 |

TABLE 1-continued

|  | CGM | ETM | HTM | VL (V) |
|---|---|---|---|---|
| COMP. EX. 1 | CG1 | 3-1 | HT1-1 | 220 |
| COMP. EX. 2 | CG2 | 3-1 | HT1-1 | 242 |
| COMP. EX. 3 | CG1 | ET13 | HT1-1 | 305 |
| COMP. EX. 4 | CG2 | ET13 | HT1-1 | 330 |
| COMP. EX. 5 | CG1 | — | HT1-1 | 478 |

Photosensitive Material for Digital Light Source (Single-Layer Type Using Electron Acceptive Compound (Hereinafter Referred to as "EAC")

Example 9

According to the same manner as that described in Example 1 except for adding 10 parts by weight of p-benzoquinone (traction potential: −0.81 V) represented by the above formula (2-1) as the electron acceptive compound (EAC), a photosensitive material for digital light source which has a single-layer type photosensitive layer was produced.

Example 10

According to the same manner as that described in Example 9 except for adding 10 parts by weight of 2,6-di-t-butyl-p-benzoquinone (traction potential: −1.31 V) represented by the above formula (2-2) in place of p-benzoquinone as the electron acceptive compound (EAC), a photosensitive material for digital light source which has a single-layer type photosensitive layer was produced.

Example 11

According to the same manner as that described in Example 9 except for adding 10 parts by weight of 3,5-dimethyl-3',5'-di-t-butyl-4,4'-diphenoquinone (traction potential: −0.86 V) represented by the above formula (3-1) in place of p-benzoquinone as the electron acceptive compound (EAC), a photosensitive material for digital light source which has a single-layer type photosensitive layer was produced.

Example 12

According to the same manner as that described in Example 9 except for adding 10 parts by weight of 3,5,3',5'-tetrakis(t-butyl)-4,4'-diphenoquinone represented by the above formula (3-2) in place of p-benzoquinone as the electron acceptive compound (EAC), a photosensitive material for digital light source which has a single-layer type photosensitive layer was produced.

Examples 13 to 16

According to the same manner as that described in Examples 9 to 12 except that 30 parts by weight of 2-oxycarbonyl-t-butyl-3-phenyl-1,4-naphthoquinone represented by the above formula (10-2) was used in place of 2-oxycarbonylethyl-3-phenyl-1,4-naphthoquinone as the electron transferring material (ETM), a photosensitive material for digital light source which has a single-layer type photosensitive layer was produced, respectively.

Examples 17 to 20

According to the same manner as that described in Examples 9 to 12 except that 30 parts by weight of 2-oxycarbonylbenzyl-3-phenyl-1,4-naphthoquinone represented by the above formula (10-3) was used in place of 2-oxycarbonylethyl-3-phenyl-1,4-naphthoquinone as the electron transferring material (ETM), a photosensitive material for digital light source which has a single-layer type photosensitive layer was produced, respectively.

Examples 21 to 24

According to the same manner as that described in Examples 9 to 12 except that 30 parts by weight of 3-methyl-2-oxycarbonybenzyl-1,4-naphthoquinone represented by the above formula (10-4) was used in place of 2-oxycarbonylethyl-3-phenyl-1,4-naphthoquinone as the electron transferring material (ETM), a photosensitive material for digital light source which has a single-layer type photosensitive layer was produced, respectively.

Comparative Examples 6 to 9

According to the same manner as that described in Examples 9 to 12 except that 30 parts by weight of 3-phenyl-1,4-naphthoquinone represented by the above formula (ET13) was used in place of 2-oxycarbonylethyl-3-phenyl-1,4-naphthoquinone as the electron transferring material (ETM), a photosensitive material for digital light source which has a single-layer type photosensitive layer was produced, respectively.

The electrophotosensitive materials of the above respective Examples and respective Comparative Examples were subjected to the above photosensitivity test I to evaluate their characteristics. The results are shown in Tables 2 to 4.

TABLE 2

|  | CGM | ETM | EAC | HTM | VL (V) |
|---|---|---|---|---|---|
| EXAMPLE 9 | CG1 | 10-1 | 2-1 | HT1-1 | 135 |
| EXAMPLE 10 | CG1 | 10-1 | 2-2 | HT1-1 | 132 |
| EXAMPLE 11 | CG1 | 10-1 | 3-1 | HT1-1 | 130 |
| EXAMPLE 12 | CG1 | 10-1 | 3-2 | HT1-1 | 128 |
| EXAMPLE 13 | CG1 | 10-2 | 2-1 | HT1-1 | 137 |
| EXAMPLE 14 | CG1 | 10-2 | 2-2 | HT1-1 | 135 |
| EXAMPLE 15 | CG1 | 10-2 | 3-1 | HT1-1 | 135 |
| EXAMPLE 16 | CG1 | 10-2 | 3-2 | HT1-1 | 131 |

TABLE 3

|  | CGM | ETM | EAC | HTM | VL (V) |
|---|---|---|---|---|---|
| EXAMPLE 17 | CG1 | 10-3 | 2-1 | HT1-1 | 130 |
| EXAMPLE 18 | CG1 | 10-3 | 2-2 | HT1-1 | 128 |
| EXAMPLE 19 | CG1 | 10-3 | 3-1 | HT1-1 | 122 |
| EXAMPLE 20 | CG1 | 10-3 | 3-2 | HT1-1 | 118 |
| EXAMPLE 21 | CG1 | 10-4 | 2-1 | HT1-1 | 130 |
| EXAMPLE 22 | CG1 | 10-4 | 2-2 | HT1-1 | 130 |
| EXAMPLE 23 | CG1 | 10-4 | 3-1 | HT1-1 | 123 |
| EXAMPLE 24 | CG1 | 10-4 | 3-2 | HT1-1 | 120 |

TABLE 4

|  | CGM | ETM | EAC | HTM | VL (V) |
|---|---|---|---|---|---|
| COMP. EX. 6 | CG1 | ET13 | 2-1 | HT1-1 | 295 |
| COMP. EX. 7 | CG1 | ET13 | 2-2 | HT1-1 | 290 |
| COMP. EX. 8 | CG1 | ET13 | 3-1 | HT1-1 | 290 |
| COMP. EX. 9 | CG1 | ET13 | 3-2 | HT1-1 | 288 |

Photosensitive Material for Digital Light Source (multi-layer type)

Example 25

100 Parts by weight of X type metal-free phthalocyanine as the charge generating material (CGM), 100 parts by weight of polyvinyl butyral as the binding resin and 2000 parts by weight of tetrahydrofuran were mixed and dispersed in a ball mill for 50 hours to prepare a coating solution for charge generating layer.

Then, this coating solution was applied on an aluminum tube as the conductive substrate by a dip coating method, followed by hot-air drying at 100° C. for 60 minutes to form a charge generating layer of 1 μm in thickness.

Then, 100 parts by weight of 2-oxycarbonylethyl-3-phenyl-1,4-naphthoquinone represented by the above formula (10-1) obtained in Synthesis Example 1 as the electron transferring material (ETM), 100 parts by weight of polycarbonate as the binding resin and 800 parts by weight of toluene were mixed and dispersed in a ball mill for 50 minutes to prepare a coating solution for a charge transferring layer.

Then, this coating solution was applied on the above charge generating layer by a dip coating method, followed by hot-air drying at 100° C. for 60 minutes to form a charge transferring layer of 20 μm in thickness, thereby producing a photosensitive material for digital light source which has a multi-layer type photosensitive layer.

Example 26

According to the same manner as that described in Example 25 except that 100 parts by weight of 2-oxycarbonyl-t-butyl-3-phenyl-1,4-naphthoquinone represented by the above formula (10-2) was used in place of 2-oxycarbonylethyl-3-phenyl-1,4-naphthoquinone as the electron transferring material (ETM), a photosensitive material for digital light source which has a multi-layer type photosensitive layer was produced.

Example 27

According to the same manner as that described in Example 25 except that 100 parts by weight of 2-oxycarbonylbenzyl-3-phenyl-1,4-naphthoquinone represented by the above formula (10-3) was used in place of 2-oxycarbonylethyl-3-phenyl-1,4-naphthoquinone as the electron transferring material (ETM), a photosensitive material for digital light source which has a multi-layer type photosensitive layer was produced.

Example 28

According to the same manner as that described in Example 25 except that 100 parts by weight of 2-oxycarbonylbenzyl-3-methyl-1,4-naphthoquinone represented by the formula (10-4) was used in place of 2-oxycarbonylethyl-3-phenyl-1,4-naphthoquinone as the electron transferring material, a photosensitive material for digital light source which has a multi-layer type photosensitive layer was produced.

Comparative Example 10

According to the same manner as that described in Example 25 except that 100 parts by weight of 3,5-dimethyl-3',5'-di-t-butyl-4,4'-diphenoquinone represented by the above formula (3-1) was used in place of 2-oxycarbonylethyl-3-phenyl-1,4-naphthoquinone as the electron transferring material, a photosensitive material for digital light source which has a multi-layer type photosensitive layer was produced.

Comparative Example 11

According to the same manner as that described in Example 25 except that 100 parts by weight of 3-phenyl-1,4-naphthoquinone represented by the above formula (ET13) was used in place of 2-oxycarbonylethyl-3-phenyl-1,4-naphthoquinone as the electron transferring material, a photosensitive material for digital light source which has a multi-layer type photosensitive layer was produced.

The electrophotosensitive materials of the above respective Examples and Comparative Examples were subjected to the above photosensitivity test I to evaluate their characteristics. The results are shown in Table 5.

TABLE 5

|  | CGM | ETM | VL (V) |
| --- | --- | --- | --- |
| EXAMPLE 25 | CG1 | 10-1 | 270 |
| EXAMPLE 26 | CG1 | 10-2 | 269 |
| EXAMPLE 27 | CG1 | 10-3 | 262 |
| EXAMPLE 28 | CG1 | 10-4 | 262 |
| COMP. EX. 10 | CG1 | 3-1 | 346 |
| COMP. EX. 11 | CG1 | ET13 | 409 |

Photosensitive Material for Analog Light Source (single-layer type)

Examples 29 to 32 and Comparative Examples 12 to 14

According to the same manner as that described in Examples 1, 3, 5 and 7 and Comparative Examples 1, 3 and 5 except for using 5 parts by weight of a compound (Ip=5.50 eV) represented by the formula (CG3a-1):

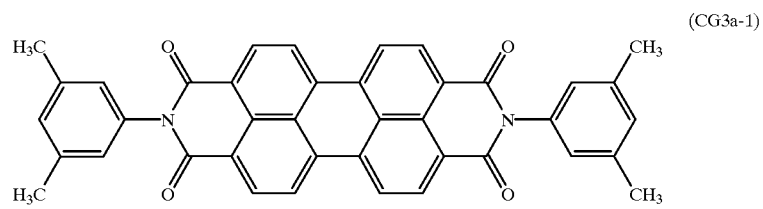

(CG3a-1)

which belongs to the perylene pigment represented by the above general formula (CG3a) in place of X type metal-free phthalocyanine as the charge generating material (CGM), a photosensitive material for analog light source which has a single-layer type photosensitive layer was produced.

The electrophotosensitive materials of the above respective Examples and respective Comparative Examples were subjected to the following photosensitivity test II to evaluate their characteristics.

Photosensitivity Test II

By using a drum sensitivity tester manufactured by GENTEC Co., a voltage was applied on the surface of the electrophotosensitive material of the respective Examples and Comparative Examples to charge the surface at +700 V. Then, white light (light intensity: 147 $\mu$W/cm$^2$) of a halogen lamp as an exposure light source was irradiated on the surface of the photosensitive material (irradiation time: 50 msec.). Further, a surface potential at the time at which 330 msec. has passed since the beginning of exposure was measured as a potential after exposure VL (V). The smaller the potential after exposure VL (V), the higher the sensitivity of the electrophotosensitive material is.

The results are shown in Table 6.

TABLE 6

|  | CGM | ETM | HTM | VL (V) |
| --- | --- | --- | --- | --- |
| EXAMPLE 29 | CG3a-1 | 10-1 | HT1-1 | 215 |
| EXAMPLE 30 | CG3a-1 | 10-2 | HT1-1 | 216 |
| EXAMPLE 31 | CG3a-1 | 10-3 | HT1-1 | 206 |
| EXAMPLE 32 | CG3a-1 | 10-4 | HT1-1 | 204 |
| COMP. EX. 12 | CG3a-1 | 3-1 | HT1-1 | 294 |
| COMP. EX. 13 | CG3a-1 | ET13 | HT1-1 | 375 |
| COMP. EX. 14 | CG3a-1 | — | HT1-1 | 521 |

Photosensitive Material for Analog Light Source (multi-layer type)

Examples 33 to 36 and Comparative Examples 15 and 16

According to the same manner as that described in Examples 25 to 28 and Comparative Examples 10 and 11 except that 100 parts by weight of the perylene pigment represented by the above formula (CG3a-1) was used in place of X type metal-free phthalocyanine as the charge generating material, a photosensitive material for analog light source which has a multi-layer type photosensitive layer was produced, respectively.

The electrophotosensitive materials of the above respective Examples and Comparative Examples were subjected to the above photosensitivity test II to evaluate their characteristics. The results are shown in Table 7.

TABLE 7

|  | CGM | ETM | VL (V) |
| --- | --- | --- | --- |
| EXAMPLE 33 | CG3a-1 | 10-1 | 300 |
| EXAMPLE 34 | CG3a-1 | 10-2 | 304 |
| EXAMPLE 35 | CG3a-1 | 10-3 | 285 |
| EXAMPLE 36 | CG3a-1 | 10-4 | 282 |
| COMP. EX. 15 | CG3a-1 | 3-1 | 386 |
| COMP. EX. 16 | CG3a-1 | ET13 | 455 |

Photosensitive Material for Digital Light Source (single-layer type)

Examples 37 and 38

According to the same manner as that described in Examples 1 and 2 except that 30 parts by weight of 2-(oxycarbonyl-4-methylphenyl)-3-phenyl-1,4-naphthoquinone represented by the above formula (10-5) obtained in Synthesis Example 4 was used in place of 2-oxycarbonylethyl-3-phenyl-1,4-naphthoquinone as the electron transferring material (ETM), a photosensitive material for digital light source which has a single-layer type photosensitive layer was produced, respectively.

Examples 39 and 40

According to the same manner as that described in Examples 1 and 2 except that 30 parts by weight of 2-(oxycarbonyl-4-isopropylphenyl)-3-phenyl-1,4-naphthoquinone represented by the above formula (10-6) was used in place of 2-oxycarbonylethyl-3-phenyl-1,4-naphthoquinone as the electron transferring material, a photosensitive material for digital light source which has a single-layer type photosensitive layer was produced, respectively.

Examples 41 and 42

According to the same manner as that described in Examples 1 and 2 except that 30 parts by weight of 2-(oxycarbonyl-4-ethylphenyl)-3-phenyl-1,4-naphthoquinone represented by the above formula (10-7) obtained in Synthesis Example 5 was used in place of 2-oxycarbonylethyl-3-phenyl-1,4-naphthoquinone as the electron transferring material, a photosensitive material for digital light source which has a single-layer type photosensitive layer was produced, respectively.

The electrophotosensitive materials of the above respective Examples were subjected to the above photosensitivity test I to evaluate their characteristics. The results are shown in Table 8.

TABLE 8

|  | CGM | ETM | HTM | VL (V) |
| --- | --- | --- | --- | --- |
| EXAMPLE 37 | CG1 | 10-5 | HT1-1 | 175 |
| EXAMPLE 38 | CG2 | 10-5 | HT1-1 | 190 |
| EXAMPLE 39 | CG1 | 10-6 | HT1-1 | 172 |
| EXAMPLE 40 | CG2 | 10-6 | HT1-1 | 190 |
| EXAMPLE 41 | CG1 | 10-7 | HT1-1 | 173 |
| EXAMPLE 42 | CG2 | 10-7 | HT1-1 | 189 |

Photosensitive Material for Digital Light Source (single-layer type using electron acceptive compound (EAC))

Examples 43 to 46

According to the same manner as that described in Examples 9 to 12 except that 30 parts by weight of 2-(oxycarbonyl-4-methylphenyl)-3-phenyl-1,4-naphthoquinone represented by the above formula (10-5) obtained in Synthesis Example 2 was used in place of 2-oxycarbonylethyl-3-phenyl-1,4-naphthoquinone as the electron transferring material, a photosensitive material for digital light source which has a single-layer type photosensitive layer was produced, respectively.

Examples 47 to 50

According to the same manner as that described in Examples 9 to 12 except that 30 parts by weight of 2-(oxycarbonyl-4-isopropylphenyl)-3-phenyl-1,4-naphthoquinone represented by the above formula (10-6) was used in place of 2-oxycarbonylethyl-3-phenyl-1,4-naphthoquinone as the electron transferring material, a photosensitive material for digital light source which has a single-layer type photosensitive layer was produced, respectively.

Examples 51 to 54

According to the same manner as that described in Examples 9 to 12 except that 30 parts by weight of 2-(oxycarbonyl-4-ethylphenyl)-3-phenyl-1,4-naphthoquinone represented by the above formula (10-7) obtained in Synthesis Example 5 was used in place of 2-oxycarbonylethyl-3-phenyl-1,4-naphthoquinone as the electron transferring material, a photosensitive material for digital light source which has a single-layer type photosensitive layer was produced, respectively.

The electrophotosensitive materials of the above respective Examples were subjected to the above photosensitivity test I to evaluate their characteristics. The results are shown in Table 9.

TABLE 9

|  | CGM | ETM | EAC | HTM | VL (V) |
|---|---|---|---|---|---|
| EXAMPLE 43 | CG1 | 10-5 | 2-1 | HT1-1 | 130 |
| EXAMPLE 44 | CG1 | 10-5 | 2-2 | HT1-1 | 129 |
| EXAMPLE 45 | CG1 | 10-5 | 3-1 | HT1-1 | 125 |
| EXAMPLE 46 | CG1 | 10-5 | 3-2 | HT1-1 | 122 |
| EXAMPLE 47 | CG1 | 10-6 | 2-1 | HT1-1 | 128 |
| EXAMPLE 48 | CG1 | 10-6 | 2-2 | HT1-1 | 128 |
| EXAMPLE 49 | CG1 | 10-6 | 3-1 | HT1-1 | 121 |
| EXAMPLE 50 | CG1 | 10-6 | 3-2 | HT1-1 | 117 |
| EXAMPLE 51 | CG1 | 10-7 | 2-1 | HT1-1 | 130 |
| EXAMPLE 52 | CG1 | 10-7 | 2-2 | HT1-1 | 128 |
| EXAMPLE 53 | CG1 | 10-7 | 3-1 | HT1-1 | 125 |
| EXAMPLE 54 | CG1 | 10-7 | 3-2 | HT1-1 | 122 |

Photosensitive Material for Digital Light Source (multi-layer type)

Example 55

According to the same manner as that described in Examples 25 except that 100 parts by weight of 2-(oxycarbonyl-4-methylphenyl)-3-phenyl-1,4-naphthoquinone represented by the above formula (10-5) obtained in Synthesis Example 2 was used in place of 2-oxycarbonylethyl-3-phenyl-1,4-naphthoquinone as the electron transferring material (ETM), a photosensitive material for digital light source which has a multi-layer type photosensitive layer was produced.

Example 56

According to the same manner as that described in Example 25 except that 100 parts by weight of 2-(oxycarbonyl-4-isopropylphenyl)-3-phenyl-1,4-naphthoquinone represented by the above formula (10-6) was used in place of 2-oxycarbonylethyl-3-phenyl-1,4-naphthoquinone as the electron transferring material, a photosensitive material for digital light source which has a multi-layer type photosensitive layer was produced.

Example 57

According to the same manner as that described in Example 25 except that 100 parts by weight of 2-(oxycarbonyl-4-ethylphenyl)-3-phenyl-1,4-naphthoquinone represented by the above formula (10-7) obtained in Synthesis Example 5 was used in place of 2-oxycarbonylethyl-3-phenyl-1,4-naphthoquinone as the electron transferring material, a photosensitive material for digital light source which has a multi-layer type photosensitive layer was produced, respectively.

The electrophotosensitive materials of the above respective Examples were subjected to the above photosensitivity test I to evaluate their characteristics. The results are shown in Table 10.

TABLE 10

|  | CGM | ETM | VL (V) |
|---|---|---|---|
| EXAMPLE 55 | CG1 | 10-5 | 266 |
| EXAMPLE 56 | CG1 | 10-6 | 259 |
| EXAMPLE 57 | CG1 | 10-7 | 266 |

Photosensitive Material for Analog Light Source (single-layer type)

Examples 58 to 60

According to the same manner as that described in Examples 37, 39 and 41 except that 5 parts by weight of the compound (Ip=5.50 eV) represented by the above formula (CG3a-1) was used in place of X type metal-free phthalocyanine as the charge generating material (CGM), a photosensitive material for analog light source which has a single-layer type photosensitive layer was produced, respectively.

The electrophotosensitive materials of the above respective Examples were subjected to the above photosensitivity test II to evaluate their characteristics. The results are shown in Table 11.

TABLE 11

|  | CGM | ETM | HTM | VL (V) |
|---|---|---|---|---|
| EXAMPLE 58 | CG3a-1 | 10-5 | HT1-1 | 210 |
| EXAMPLE 59 | CG3a-1 | 10-6 | HT1-1 | 209 |
| EXAMPLE 60 | CG3a-1 | 10-7 | HT1-1 | 208 |

Photosensitive Material for Analog Light Source (multi-layer type)

Examples 61 to 63

According to the same manner as that described in Examples 55 to 57 except that 100 parts by weight of the perylene pigment represented by the above formula (CG3a-1) was used in place of X type metal-free phthalocyanine as the charge generating material, a photosensitive material for analog light source which has a multi-layer type photosensitive layer was produced, respectively.

The electrophotosensitive materials of the above respective Examples were subjected to the above photosensitivity test II to evaluate their characteristics. The results are shown in Table 12.

TABLE 12

|  | CGM | ETM | VL (V) |
|---|---|---|---|
| EXAMPLE 61 | CG3a-1 | 10-5 | 290 |
| EXAMPLE 62 | CG3a-1 | 10-6 | 290 |
| EXAMPLE 63 | CG3a-1 | 10-7 | 290 |

Photosensitive Material for Digital Light Source (single-layer type)

Examples 64 and 65

According to the same manner as that described in Examples 1 and 2 except that 30 parts by weight of 2-benzoyl-3-phenyl-1,4-naphthoquinone represented by the above formula (1-1) obtained in Synthesis Example 6 was used in place of 2-oxycarbonylethyl-3-phenyl-1,4-naphthoquinone as the electron transferring material (ETM), a photosensitive material for digital light source which has a single-layer type photosensitive layer was produced, respectively.

Examples 66 and 67

According to the same manner as that described in Examples 1 and 2 except that 30 parts by weight of 2-(4-ethylbenzoyl)-3-phenyl-1,4-naphthoquinone represented by the above formula (1-2) was used in place of 2-oxycarbonylethyl-3-phenyl-1,4-naphthoquinone as the electron transferring material, a photosensitive material for digital light source which has a single-layer type photosensitive layer was produced, respectively.

Examples 68 and 69

According to the same manner as that described in Examples 1 and 2 except that 30 parts by weight of 2-benzoyl-3-(4-isopropylphenyl)-1,4-naphthoquinone represented by the above formula (1-3) obtained in Synthesis Example 7 was used in place of 2-oxycarbonylethyl-3-phenyl-1,4-naphthoquinone as the electron transferring material, a photosensitive material for digital light source which has a single-layer type photosensitive layer was produced, respectively.

Examples 70 and 71

According to the same manner as that described in Examples 1 and 2 except that 30 parts by weight of 2-benzoyl-3-methyl-1,4-naphthoquinone represented by the above formula (1-4) obtained in Synthesis Example 8 was used in place of 2-oxycarbonylethyl-3-phenyl-1,4-naphthoquinone as the electron transferring material, a photosensitive material for digital light source which has a single-layer type photosensitive layer was produced, respectively.

The electrophotosensitive materials of the above respective Examples were subjected to the above photosensitivity test I to evaluate their characteristics. The results are shown in Table 13.

TABLE 13

|  | CGM | ETM | HTM | VL (V) |
| --- | --- | --- | --- | --- |
| EXAMPLE 64 | CG1 | 1-1 | HT1-1 | 185 |
| EXAMPLE 65 | CG2 | 1-1 | HT1-1 | 205 |
| EXAMPLE 66 | CG1 | 1-2 | HT1-1 | 182 |
| EXAMPLE 67 | CG2 | 1-2 | HT1-1 | 207 |
| EXAMPLE 68 | CG1 | 1-3 | HT1-1 | 192 |
| EXAMPLE 69 | CG2 | 1-3 | HT1-1 | 206 |
| EXAMPLE 70 | CG1 | 1-4 | HT1-1 | 186 |
| EXAMPLE 71 | CG2 | 1-4 | HT1-1 | 205 |

Photosensitive Material for Digital Light Source (single-layer type using electron acceptive compound (EAC))

Examples 72 to 75

According to the same manner as that described in Examples 9 to 12 except that 30 parts by weight of 2-benzoyl-3-phenyl-1,4-naphthoquinone represented by the above formula (1-1) obtained in Synthesis Example 3 was used in place of 2-oxycarbonylethyl-3-phenyl-1,4-naphthoquinone as the electron transferring material (ETM), a photosensitive material for digital light source which has a single-layer type photosensitive layer was produced, respectively.

Examples 76 to 79

According to the same manner as that described in Examples 9 to 12 except that 30 parts by weight of 2-(4-ethylbenzoyl)-3-phenyl-1,4-naphthoquinone represented by the above formula (1-2) was used in place of 2-oxycarbonylethyl-3-phenyl-1,4-naphthoquinone as the electron transferring material, a photosensitive material for digital light source which has a single-layer type photosensitive layer was produced, respectively.

Examples 80 to 83

According to the same manner as that described in Examples 9 to 12 except that 30 parts by weight of 2-benzoyl-3-(4-isopropylphenyl)-1,4-naphthoquinone represented by the above formula (1-3) obtained in Synthesis Example 7 was used in place of 2-oxycarbonylethyl-3-phenyl-1,4-naphthoquinone as the electron transferring material, a photosensitive material for digital light source which has a single-layer type photosensitive layer was produced, respectively.

Examples 84 to 87

According to the same manner as that described in Examples 9 to 12 except that 30 parts by weight of 2-benzoyl-3-methyl-1,4-naphthoquinone represented by the above formula (1-4) obtained in Synthesis Example 8 was used in place of 2-oxycarbonylethyl-3-phenyl-1,4-naphthoquinone as the electron transferring material, a photosensitive material for digital light source which has a single-layer type photosensitive layer was produced, respectively.

The electrophotosensitive materials of the above respective Examples were subjected to the above photosensitivity test I to evaluate their characteristics. The results are shown in Tables 14 and 15.

TABLE 14

|  | CGM | ETM | EAC | HTM | VL (V) |
| --- | --- | --- | --- | --- | --- |
| EXAMPLE 72 | CG1 | 1-1 | 2-1 | HT1-1 | 142 |
| EXAMPLE 73 | CG1 | 1-1 | 2-2 | HT1-1 | 138 |
| EXAMPLE 74 | CG1 | 1-1 | 3-1 | HT1-1 | 136 |
| EXAMPLE 75 | CG1 | 1-1 | 3-2 | HT1-1 | 133 |
| EXAMPLE 76 | CG1 | 1-2 | 2-1 | HT1-1 | 139 |
| EXAMPLE 77 | CG1 | 1-2 | 2-2 | HT1-1 | 137 |
| EXAMPLE 78 | CG1 | 1-2 | 3-1 | HT1-1 | 135 |
| EXAMPLE 79 | CG1 | 1-2 | 3-2 | HT1-1 | 129 |

TABLE 15

|  | CGM | ETM | EAC | HTM | VL (V) |
| --- | --- | --- | --- | --- | --- |
| EXAMPLE 80 | CG1 | 1-3 | 2-1 | HT1-1 | 146 |
| EXAMPLE 81 | CG1 | 1-3 | 2-2 | HT1-1 | 142 |
| EXAMPLE 82 | CG1 | 1-3 | 3-1 | HT1-1 | 140 |
| EXAMPLE 83 | CG1 | 1-3 | 3-2 | HT1-1 | 138 |
| EXAMPLE 84 | CG1 | 1-4 | 2-1 | HT1-1 | 142 |

TABLE 15-continued

|  | CGM | ETM | EAC | HTM | VL (V) |
|---|---|---|---|---|---|
| EXAMPLE 85 | CG1 | 1-4 | 2-2 | HT1-1 | 142 |
| EXAMPLE 86 | CG1 | 1-4 | 3-1 | HT1-1 | 140 |
| EXAMPLE 87 | CG1 | 1-4 | 3-2 | HT1-1 | 135 |

Photosensitive Material for Digital Light Source
(multi-layer type)

Example 88

According to the same manner as that described in Example 25 except that 100 parts by weight of 2-benzoyl-3-phenyl-1,4-naphthoquinone represented by the above formula (1-1) obtained in Synthesis Example 3 was used in place of 2-oxycarbonylethyl-3-phenyl-1,4-naphthoquinone as the electron transferring material (ETM), a photosensitive material for digital light source which has a multi-layer type photosensitive layer was produced.

Example 89

According to the same manner as that described in Example 25 except that 100 parts by weight of 2-(4-ethylbenzoyl)-3-phenyl-1,4-naphthoquinone represented by the above formula (1-2) was used in place of 2-oxycarbonylethyl-3-phenyl-1,4-naphthoquinone as the electron transferring material, a photosensitive material for digital light source which has a multi-layer type photosensitive layer was produced.

Example 90

According to the same manner as that described in Example 25 except that 100 parts by weight of 2-benzoyl-3-(4-isopropylphenyl)-1,4-naphthoquinone represented by the above formula (1-3) obtained in Synthesis Example 7 was used in place of 2-oxycarbonylethyl-3-phenyl-1,4-naphthoquinone as the electron transferring material, a photosensitive material for digital light source which has a multi-layer type photosensitive layer was produced.

Example 91

According to the same manner as that described in Example 25 except that 100 parts by weight of 2-benzoyl-3-methyl-1,4-naphthoquinone represented by the above formula (1-4) obtained in Synthesis Example 8 was used in place of 2-oxycarbonylethyl-3-phenyl-1,4-naphthoquinone as the electron transferring material, a photosensitive material for digital light source which has a multi-layer type photosensitive layer was produced.

The electrophotosensitive materials of the above respective Examples were subjected to the above photosensitivity test I to evaluate their characteristics. The results are shown in Table 16.

TABLE 16

|  | CGM | ETM | VL (V) |
|---|---|---|---|
| EXAMPLE 88 | CG1 | 1-1 | 285 |
| EXAMPLE 89 | CG1 | 1-2 | 280 |
| EXAMPLE 90 | CG1 | 1-3 | 290 |
| EXAMPLE 91 | CG1 | 1-4 | 287 |

Photosensitive Material for Analog Light Source
(single-layer type)

Examples 92 to 95

According to the same manner as that described in Examples 64, 66, 68 and 70 except that 5 parts by weight of the compound (Ip=5.50 eV) represented by the above formula (CG3a-1) was used in place of X type metal-free phthalocyanine as the charge generating material, a photosensitive material for analog light source which has a single-layer type photosensitive layer was produced, respectively.

The electrophotosensitive materials of the above respective Examples were subjected to the above photosensitivity test II to evaluate their characteristics. The results are shown in Table 17.

TABLE 17

|  | CGM | ETM | HTM | VL (V) |
|---|---|---|---|---|
| EXAMPLE 92 | CG3a-1 | 1-1 | HT1-1 | 225 |
| EXAMPLE 93 | CG3a-1 | 1-2 | HT1-1 | 219 |
| EXAMPLE 94 | CG3a-1 | 1-3 | HT1-1 | 228 |
| EXAMPLE 95 | CG3a-1 | 1-4 | HT1-1 | 227 |

Photosensitive Material for Analog Light Source
(multi-layer type)

Examples 96 to 99

According to the same manner as that described in Examples 88 to 91 except that 100 parts by weight of the perylene pigment represented by the above formula (CG3a-1) was used in place of X type metal-free phthalocyanine as the charge generating material, a photosensitive material for analog light source which has a multi-layer type photosensitive layer was produced, respectively.

The electrophotosensitive materials of the above respective Examples were subjected to the above photosensitivity test II to evaluate their characteristics. The results are shown in Table 18.

TABLE 18

|  | CGM | ETM | VL (V) |
|---|---|---|---|
| EXAMPLE 96 | CG3a-1 | 1-1 | 310 |
| EXAMPLE 97 | CG3a-1 | 1-2 | 311 |
| EXAMPLE 98 | CG3a-1 | 1-3 | 315 |
| EXAMPLE 99 | CG3a-1 | 1-4 | 308 |

Evaluation of Photostability of Photosensitive Material

A half-life exposure $E_{1/2}$ (I) of the photosensitive material of Example 1 using 2-oxycarbonylethyl-3-phenyl-1,4-naphthoquinone represented by the above formula (10-1) as the electron transferring material and photosensitive material of Example 64 using 2-benzoyl-3-phenyl-1,4-naphthoquinone represented by the above formula (1-1) as the electron transferring material was respectively measured, using the drum sensitivity tester manufactured by GENTEC Co. used in the above photosensitivity test I.

Next, after light having an intensity of 1000 lux was irradiated to the surface of the above both photosensitive materials for 30 minutes, using a white fluorescent tube, the half-life exposure $E_{1/2}$ (E) of the above both photosensitive materials was respectively measured again, using the above drum sensitivity tester.

Then, an increase % of the above half-life exposure was determined from the above half-life exposure $E_{1/2}$ (I) and half-life exposure $E_{1/2}$ (E), according to the following formula, to evaluate the photostability of the photosensitive material.

$$\text{Increased Rate } (\%) = \frac{E_{1/2}(E)}{E_{1/2}(I)} \times 100$$

The results are shown in Table 19.

TABLE 19

|  | INCREASE (%) |
|---|---|
| EXAMPLE 1 | 106.3 |
| EXAMPLE 64 | 102.1 |

Measurement of Glass Transition Temperature of Photosensitive Layer

A glass transition temperature of the photosensitive layer of the photosensitive material of Example 1 using 2-oxycarbonylethyl-3-phenyl-1,4-naphthoquinone represented by the above formula (10-1), the photosensitive material of Example 37 using 2-(oxycarbonyl-4-methylphenyl)-3-phenyl-1,4-naphthoquinone represented by the above formula (10-5) and photosensitive material of Example 64 using 2-benzoyl-3-phenyl-1,4-naphthoquinone represented by the above formula (1-1), as the electron transferring material, was respectively measured. The results are shown in Table 20.

TABLE 20

|  | CLASS TRANSITION TEMP. |
|---|---|
| EXAMPLE 1 | 52° C. |
| EXAMPLE 37 | 58° C. |
| EXAMPLE 64 | 62° C. |

Synthesis of Polyester Resin

Using dimethyl terephthalate (10.68 kg, 55 mol), 9,9-bis[4-(2-hydroxyethoxy)phenyl]fluorene (16.88 kg, 38.5 mol) and ethylene glycol (7.2 kg, 116 mol) as the raw material and calcium acetate (15.99 g, 0.091 mol) as the catalyst, these compounds were introduced in a reaction tank and then gradually heated from 190 to 230° C. with stirring according to a conventional method to conduct a transesterification. After a predetermined amount of methanol was removed out of the system, germanium oxide (6.9 g, 0.066 mol) as the polymerization catalyst and trimethyl phosphate (14 g, 0.1 mol) as the agent for preventing coloring were introduced. Then, the temperature of the heating tank was adjusted to 280° C. and the vacuum degree was adjusted to not more than 1 Torr by gradually heating and evacuating while drawing ethylene glycol formed. This condition was maintained until the viscosity increased to reach a predetermined stirring torque and, about 2 hours after reaching, the reaction was terminated and the reaction product was extruded into water to obtain a pellet of a polyester resin.

The intrinsic viscosity of this polyester resin was 0.5 dl/g and the glass transition temperature Tg was 145° C.

Photosensitive Material for Digital Light Source (single-layer type)

Examples 100 and 101

According to the same manner as that described in Examples 64 and 65 except that 100 parts by weight of the polyester resin synthesized above, which is a substantially linear polymer was used in place of polycarbonate as the binding resin, a photosensitive material for digital light source which has a single-layer type photosensitive layer was produced, respectively.

The electrophotosensitive materials thus obtained were subjected to the above photosensitivity test I to evaluate their characteristics. The results are shown in Table 21.

TABLE 21

|  | CGM | ETM | HTM | VL (V) |
|---|---|---|---|---|
| EXAMPLE 100 | CG1 | 1-1 | HT1-1 | 170 |
| EXAMPLE 101 | CG2 | 1-1 | HT1-1 | 189 |

Photosensitive Material for Digital Light Source (single-layer type using electron acceptive compound (EAC))

Examples 102 to 105

According to the same manner as that described in Examples 72 to 75 except that 100 parts by weight of the same polyester resin as that used in Examples 100 and 101 was used in place of polycarbonate as the binding resin, a photosensitive material for digital light source which has a single-layer type photosensitive layer was produced, respectively.

The electrophotosensitive materials thus obtained were subjected to the above photosensitivity test I to evaluate their characteristics. The results are shown in Table 22.

TABLE 22

|  | CGM | ETM | EAC | HTM | VL (V) |
|---|---|---|---|---|---|
| EXAMPLE 102 | CG1 | 1-1 | 2-1 | HT1-1 | 136 |
| EXAMPLE 103 | CG1 | 1-1 | 2-2 | HT1-1 | 130 |
| EXAMPLE 104 | CG1 | 1-1 | 3-1 | HT1-1 | 125 |
| EXAMPLE 105 | CG1 | 1-1 | 3-2 | HT1-1 | 122 |

Photosensitive Material for Digital Light Source (multi-layer type)

Example 106

According to the same manner as that described in Example 88 except that 100 parts by weight of the same polyester resin as that used in Examples 100 and 101 was used in place of polycarbonate as the binding resin, a photosensitive material for digital light source which has a multi-layer type photosensitive layer was produced.

The electrophotosensitive material thus obtained was subjected to the above photosensitivity test I to evaluate its characteristics. The results are shown in Table 23.

TABLE 23

|  | CGM | ETM | VL (V) |
|---|---|---|---|
| EXAMPLE 106 | CG1 | 1-1 | 266 |

Photosensitive Material for Analog Light Source (single-layer type)

Example 107

According to the same manner as that described in Example 100 except that 5 parts by weight of the compound (Ip=5.50 eV) represented by the above formula (CG3a-1) was used in place of X type metal-free phthalocyanine as the charge generating material (CGM), a photosensitive material for analog light source which has a single-layer type photosensitive layer was produced. The electrophotosensitive material thus obtained was subjected to the above photosensitivity test II to evaluate its characteristics. The results are shown in Table 24.

TABLE 24

|  | CGM | ETM | HTM | VL (V) |
|---|---|---|---|---|
| EXAMPLE 107 | CG3a-1 | 1-1 | HT-1 | 208 |

Photosensitive Material for Analog Light Source (multi-layer type)

Example 108

According to the same manner as that described in Example 106 except that 100 parts by weight of the perylene pigment represented by the above formula (CG3a-1) was used in place of X type metal-free phthalocyanine as the charge generating material, a photosensitive material for analog light source which has a multi-layer type photosensitive layer was produced.

The electrophotosensitive material thus obtained was subjected to the above photosensitivity test II to evaluate its sensitivity characteristics. The results are shown in Table 25.

TABLE 25

|  | CGM | ETM | VL (V) |
|---|---|---|---|
| EXAMPLE 108 | CG3a-1 | 1-1 | 295 |

Examples 109 to 126

According to the same manner as that described in Examples 1, 2, 5, 6, 41 and 64, except that phenanthrylenedimethyl derivatives represented by the following formulas (HT8-1) to (HT8-3) were used in place of the compound represented by the formula (HT1-1) as the hole transferring material (HTM) and, in Examples 115 to 122, the compound represented by the above formula (2-2) or (3-2) was used as the electron acceptive compound (EAC) in addition to the above hole transferring materials (HT8-l) to (HT8-3), a photosensitive material for digital light source which has a single-layer type photosensitive layer was produced, respectively.

Comparative Examples 17 to 19

According to the same manner as that described in Comparative Example 1 except that phenanthrylenedimethyl derivatives represented by the following formulas (HT8-1) to (HT8-3) were used in place of the compound represented by the formula (HT1-1) as the hole transferring material (HTM), a photosensitive material for digital light source which has a single-layer type photosensitive layer was produced, respectively.

The respective photosensitive materials obtained in these Examples 109 to 126 and Comparative Examples 17 to 19 were subjected to the same "photosensitivity test I" as that of Example 1 to evaluate their potentials after exposure VL.

Electric Characteristics Test After Repeatedly Forming Images

The respective photosensitive materials were used for a facsimile for plain paper (Model LDC-650, manufactured by Mita Industrial Co., Ltd.) and, after the image was formed 10,000 times, a surface potential was measured using the same drum sensitivity tester as that used in the above photosensitivity test I and a difference $\Delta V_0$ between the resultant surface potential and an initial surface potential before formation of the image was determined, respectively.

Wear Resistance Test

The respective photosensitive materials were fit with an image unit of a facsimile for plain paper (the aforesaid Model LDC-650) and, after rotating 150,000 times without passing a paper through it, a change in thickness of the photosensitive layer was determined, respectively.

The results are shown in Table 26.

TABLE 26

|  | CGM | ETM | HTM | EAC | VL (V) | $\Delta V_0$ | AMOUNT OF WEAR ($\mu$m) |
|---|---|---|---|---|---|---|---|
| EXAMPLE 109 | CG1 | 10-1 | HT8-1 | — | 176 | −37 | 3.1 |
| EXAMPLE 110 | CG1 | 10-1 | HT8-2 | — | 172 | −35 | 3.2 |
| EXAMPLE 111 | CG1 | 10-1 | HT8-3 | — | 176 | −33 | 3.0 |
| EXAMPLE 112 | CG1 | 10-3 | HT8-1 | — | 167 | −37 | 3.0 |
| EXAMPLE 113 | CGI | 10-7 | HT8-1 | — | 171 | −35 | 3.2 |
| EXAMPLE 114 | CG1 | 1-1 | HT8-1 | — | 183 | −33 | 2.9 |
| EXAMPLE 115 | CG1 | 10-1 | HT8-1 | 2-2 | 128 | −33 | 3.1 |
| EXAMPLE 116 | CG1 | 10-1 | HT8-1 | 3-2 | 117 | −35 | 3.0 |
| EXAMPLE 117 | CGI | 10-3 | HT8-1 | 2-2 | 122 | −33 | 3.2 |
| EXAMPLE 118 | CG1 | 10-3 | HT8-1 | 3-2 | 116 | −35 | 3.0 |
| EXAMPLE 119 | CG1 | 10-1 | HT8-2 | 2-2 | 129 | −37 | 3.1 |
| EXAMPLE 120 | CG1 | 10-1 | HT8-2 | 3-2 | 119 | −28 | 3.2 |
| EXAMPLE 121 | CG1 | 10-3 | HT8-2 | 2-2 | 129 | −36 | 3.2 |
| EXAMPLE 122 | CG1 | 10-3 | HT8-2 | 3-2 | 124 | −32 | 3.2 |
| EXAMPLE 123 | CG2 | 10-1 | HT8-1 | — | 191 | −40 | 3.0 |
| EXAMPLE 124 | CG2 | 10-3 | HT8-1 | — | 183 | −36 | 2.9 |
| EXMMPLE 125 | CG2 | 10-1 | HT8-2 | — | 191 | −32 | 3.0 |
| EXAMPLE 126 | CG2 | 10-3 | HT8-2 | — | 182 | −34 | 3.0 |
| COMP. EX. 17 | CG1 | 3-1 | HT8-1 | — | 217 | −77 | 4.8 |

TABLE 26-continued

| | CGM | ETM | HTM | EAC | VL (V) | $\Delta V_0$ | AMOUNT OF WEAR ($\mu$m) |
|---|---|---|---|---|---|---|---|
| COMP. EX. 18 | CG1 | 3-1 | HT8-2 | — | 218 | −79 | 4.5 |
| COMP. EX. 19 | CG1 | 3-1 | HT8-3 | — | 217 | −88 | 4.7 |

We claim:

1. An electrophotosensitive material comprising a conductive substrate and a photosensitive layer containing a naphthoquinone derivative represented by the formula (1)

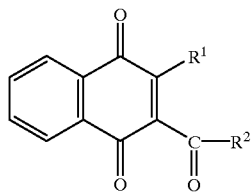
(1)

wherein $R^1$ is an unsubstituted or substituted alkyl group, or an unsubstituted or substituted aryl group, and $R^2$ is an unsubstituted or substituted alkyl group, an unsubstituted or substituted aryl group, or a group represented by a formula (1a):

wherein $R^3$ is an unsubstituted or substituted alkyl group, or an unsubstituted or substituted aryl group, said photosensitive layer being provided on said conductive substrate.

2. An electrophotosensitive material according to claim 1, wherein the photosensitive layer also contains an electron acceptive compound having a traction potential of −0.8 to −1.4 V.

3. The electrophotosensitive material according to claim 1, wherein said photosensitive layer is a single photosensitive layer comprising a charge generating material, an electron transferring material, a hole transferring material and a binding resin, and said electron transferring material is said naphthoquinone derivative represented by said formula (1).

4. An electrophotosensitive material according to claim 3, wherein the hole transferring material is a phenanethrylenediamine derivative represented by the general formula (HT8):

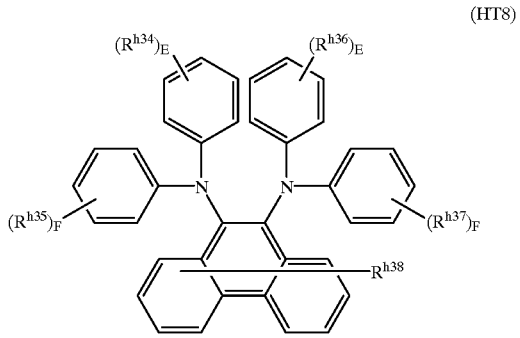
(HT8)

wherein $R^{h34}$, $R^{h35}$, $R^{h36}$ and $R^{h37}$ are the same or different and indicate a halogen atom, an alkyl group, an aryl group, an aralkyl group or an alkoxy group; $R^{h38}$ is a hydrogen atom, a halogen atom, an alkyl group or an alkoxy group; and E and F indicate an integer of 0 to 2.

5. The electrophotosensitive material according to claim 1, wherein said photosensitive layer comprises a charge generating layer comprising a charge generating material and a binding resin, and a charge transferring layer comprising an electron transferring material and a binding resin, said electron transferring material being the naphthoquinone derivative represented by said formula (1).

6. The electrophotosensitive material as defined in claim 1 wherein said naphthoquinone derivative is represented by a formula:

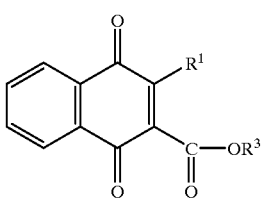
(10)

wherein $R^1$ is an aryl group or an alkyl group,
wherein $R^3$ is an alkyl group with a phenyl substituent or a phenyl group with an alkyl substituent, and
wherein when $R^1$ is an alkyl group then $R^3$ is an alkyl group with a phenyl substituent.

7. The electrophotosensitive material defined in claim 6 wherein said alkyl group of $R^1$ has 1 to 6 carbon atoms; wherein said alkyl substituent on said phenyl group of $R^3$ has 1 to 6 carbon atoms; and
wherein said alkyl group with a phenyl substituent of $R^3$ has 1 to 6 carbon atoms.

8. The electrophotosensitive material as defined in claim 7
wherein said alkyl group with a phenyl substituent of $R^3$ is a methyl group.

9. The electrophotosensitive material defined in claim 8 wherein said alkyl group of $R^1$ is a methyl group.

10. The electrophotosensitive material defined in claim 9 wherein the naphthoquinone derivative is

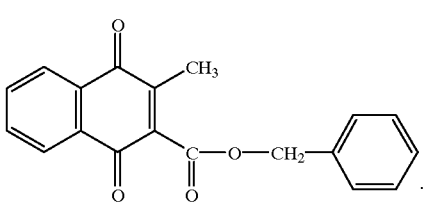
(10-4)

11. The electrophotosensitive material defined in claim 9 wherein said aryl group of $R^1$ is a phenyl group.

12. The electrophotosensitive material as defined in claim 11 wherein said alkyl substituent on the phenyl group of $R^3$ is a methyl group, an ethyl group, or an isopropyl group.

13. The electrophotosensitive material as defined in claim 12 wherein the naphthoquinone derivative is

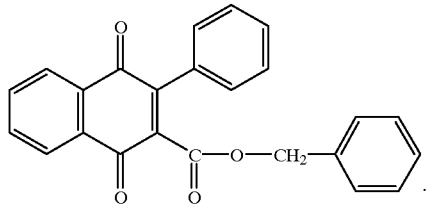
(10-3)

14. The electrophotosensitive material defined in claim 12 wherein said naphthoquinone derivative is represented by a formula:

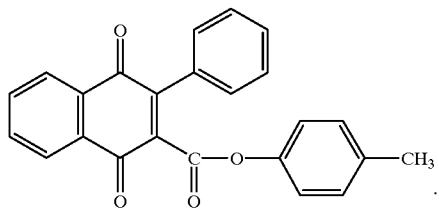
(10-5)

15. The electrophotosensitive material defined in claim 12 wherein said naphthoquinone derivative is represented by a formula:

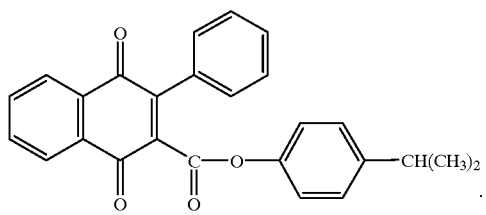
(10-6)

16. The electrophotosensitive material defined in claim 12 wherein said naphthoquinone derivative is represented by a formula:

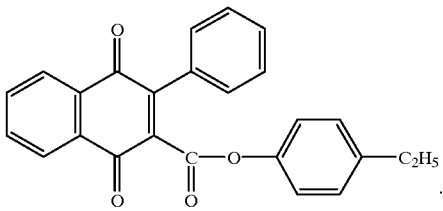
(10-7)

17. The electrophotosensitive material defined in claim 1 wherein said naphthoquinone derivative is represented by a formula:

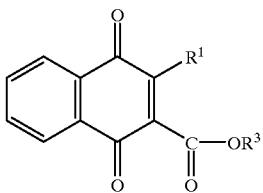
(10)

wherein $R^1$ is an unsubstituted phenyl group; and wherein $R^3$ is a phenyl group substituted with an alkyl substituent or with an aryl substituent.

18. The electrophotosensitive material defined in claim 1 wherein $R^1$ is an unsubstituted alkyl or an unsubstituted aryl group, and wherein $R^2$ is an unsubstituted phenyl group.

19. A method of making the electrophotosensitive material as defined in claim 3 comprising mixing said electron transferring material, said charge generating material, said hole transferring material and said binding resin in a suitable solvent to form a coating material, and applying said coating material on said conductive substrate to form said electrophotosensitive material.

20. A method of making the electrophotosensitive material as defined in claim 5 comprising applying said charge generating layer on said conductive substrate, and applying said electron transferring layer on said charge generating layer to form said electrophotosensitive material.

* * * * *